(12) United States Patent
Yokomizo et al.

(10) Patent No.: US 11,504,460 B2
(45) Date of Patent: *Nov. 22, 2022

(54) BLOOD TREATMENT FILTER

(71) Applicant: ASAHI KASEI MEDICAL CO., LTD., Tokyo (JP)

(72) Inventors: Tomohisa Yokomizo, Tokyo (JP); Tomoko Uchiyama, Tokyo (JP)

(73) Assignee: ASAHI KASEI MEDICAL CO., LTD., Tokyo (JP)

( * ) Notice: Subject to any disclaimer, the term of this patent is extended or adjusted under 35 U.S.C. 154(b) by 19 days.

This patent is subject to a terminal disclaimer.

(21) Appl. No.: 16/929,717

(22) Filed: Jul. 15, 2020

(65) Prior Publication Data

US 2020/0345921 A1 Nov. 5, 2020

Related U.S. Application Data

(63) Continuation of application No. 15/124,167, filed as application No. PCT/JP2015/056938 on Mar. 10, 2015, now Pat. No. 10,842,927.

(30) Foreign Application Priority Data

Mar. 10, 2014 (JP) ................................. 2014-046554

(51) Int. Cl.
   *A61M 1/36* (2006.01)
   *A61M 1/02* (2006.01)
   *B01D 63/02* (2006.01)

(52) U.S. Cl.
   CPC ........ *A61M 1/3636* (2014.02); *A61M 1/0218* (2014.02); *A61M 1/3633* (2013.01); *B01D 63/02* (2013.01); *A61M 2202/0439* (2013.01)

(58) Field of Classification Search
   CPC ........ A61M 2202/0439; A61M 1/3636; A61M 1/3633; A61M 1/0218; A61M 2202/0042;
   (Continued)

(56) References Cited

U.S. PATENT DOCUMENTS

| 4,985,153 A | 1/1991 | Kuroda et al. |
| 5,269,946 A | 12/1993 | Goldhaber et al. |

(Continued)

FOREIGN PATENT DOCUMENTS

| CN | 102205154 | 10/2011 |
| CN | 102821795 | 12/2012 |

(Continued)

OTHER PUBLICATIONS

Search Report issued in European Patent Office (EPO) Patent Application No. 15761409.0, dated Feb. 7, 2017.
(Continued)

*Primary Examiner* — Bobby Ramdhanie
*Assistant Examiner* — Donovan Bui-Huynh
(74) *Attorney, Agent, or Firm* — Greenblum & Bernstein, P.L.C.

(57) ABSTRACT

A blood treatment filter comprising a filter element, an inlet-side flexible container and an outlet-side flexible container, an inlet port, and a tubular outlet port, further comprises: an outlet-side frame sheet disposed between the filter element and the outlet-side flexible container; a first seal portion provided by sealing at least the filter element and the outlet-side frame sheet in a belt-shaped manner; and an annular second seal portion provided to surround the first seal portion, wherein on an outlet side of the filter element, a valley portion is formed at the first seal portion, the outlet port includes a protruding portion that protrudes to an inside of the container, and the protruding portion is provided with an opening at least a part of which overlaps with the first seal
(Continued)

portion and which can communicate with a gap region formed by the valley portion.

17 Claims, 11 Drawing Sheets

(58) Field of Classification Search
CPC .... A61M 2202/005; A61M 2202/0057; A61M 2202/0415; A61M 2202/0427; A61M 1/02; A61M 1/0222; A61M 1/0231; A61M 1/0281; A61M 1/1631; A61M 1/1652; A61M 1/262; A61M 1/265; A61M 1/30; A61M 1/302; A61M 1/303; A61M 1/34; A61M 1/3406; A61M 1/3496; A61M 1/3603; A61M 1/3635; A61M 1/3652; A61M 1/3686; A61M 1/3693; A61M 1/38; A61M 2206/20; B29C 66/71; B29C 65/04; B29C 66/1122; B29C 66/53262; B29C 66/723; B29C 66/72341; B29C 66/8322; B29C 66/83221; B29C 66/92651; B29C 66/929; B29C 66/949; Y10T 29/49826; Y10T 156/10; B01D 39/1623; B01D 63/02; B01D 2239/0622; B01D 2239/0627; B01D 2239/065; B01D 2239/0668; B01D 2239/1216; B01D 29/012; B01D 29/05; B01D 29/58; B01D 29/908; B01D 39/18; B01D 39/2017; B01D 61/18; B01D 63/08; B01D 63/081; B01D 69/12; B29K 2023/12; B29K 2027/06; B29K 2067/00; B29K 2077/00; A61L 2/0017; B29L 2009/00; B29L 2031/14; B29L 2031/7148
See application file for complete search history.

(56) References Cited

U.S. PATENT DOCUMENTS

| | | | |
|---|---|---|---|
| 5,403,272 A | 4/1995 | Deniega | |
| 6,032,807 A | 3/2000 | Sternberg et al. | |
| 6,168,718 B1* | 1/2001 | Sutter | B01D 63/081 |
| | | | 210/436 |
| 6,221,264 B1* | 4/2001 | Ishida | A61M 1/0218 |
| | | | 604/408 |
| 6,367,634 B1* | 4/2002 | Lynn | B01D 29/012 |
| | | | 210/489 |
| 7,641,794 B2* | 1/2010 | Oka | A61M 1/3633 |
| | | | 210/259 |
| 2004/0251195 A1* | 12/2004 | Oka | A61M 1/3633 |
| | | | 210/489 |
| 2006/0049097 A1 | 3/2006 | Cavallini et al. | |
| 2008/0223776 A1 | 9/2008 | Sumian et al. | |
| 2009/0071905 A1* | 3/2009 | Goudaliez | A61M 1/3686 |
| | | | 210/651 |
| 2010/0051533 A1 | 3/2010 | Oka et al. | |
| 2011/0192798 A1 | 8/2011 | Goudaliez et al. | |
| 2011/0240549 A1* | 10/2011 | Andou | A61M 1/3633 |
| | | | 210/435 |
| 2012/0067810 A1 | 3/2012 | Yokomizo et al. | |
| 2012/0067811 A1* | 3/2012 | Yokomizo | A61M 1/3636 |
| | | | 210/450 |
| 2014/0144832 A1 | 5/2014 | Yokomizo et al. | |
| 2014/0374338 A1* | 12/2014 | Calderon | A61M 1/3635 |
| | | | 210/435 |
| 2016/0235904 A1* | 8/2016 | Yokomizo | A61M 1/1631 |
| 2019/0343995 A1* | 11/2019 | Iida | A61M 1/0209 |

FOREIGN PATENT DOCUMENTS

| | | |
|---|---|---|
| CN | 102861365 | 1/2013 |
| EP | 0526678 | 2/1993 |
| EP | 0 953 361 | 11/1999 |
| EP | 1 258 261 | 11/2002 |
| EP | 1300168 | 4/2003 |
| FR | 2 845 276 | 4/2004 |
| JP | 01-320064 | 12/1989 |
| JP | 07-267871 | 10/1995 |
| JP | 11-216179 | 8/1999 |
| JP | 2003-512093 | 4/2003 |
| JP | 2003-180822 | 7/2003 |
| JP | 2003-521358 | 7/2003 |
| JP | 2007-252463 | 10/2007 |
| JP | 5297463 | 9/2013 |
| WO | 92/20428 | 11/1992 |
| WO | 95/017236 | 6/1995 |
| WO | 95/17237 | 6/1995 |
| WO | 01/074158 | 10/2001 |
| WO | 2007/042644 | 4/2007 |
| WO | 2010/026891 | 3/2010 |
| WO | 2011/122564 | 10/2011 |
| WO | 2012/039400 | 3/2012 |
| WO | 2012/039402 | 3/2012 |

OTHER PUBLICATIONS

International Search Report issued in PCT/JP2015/056938, dated Jun. 6, 2015.
International Preliminary Report on Patentability issued in PCT/JP2015/056938, dated Sep. 22, 2016.
MacoPharma P-CAPT Brochure entitled "Transfusion Safety of Blood Products", 2007.
P-CAPT drawing entitled/labeled "PSE3080XB", 2009.
Purchase Order entitled/labeled "NHS Blood and Transplant", 2007.
Invoice entitled/labeled "Invoice No. 137204", 2007.
Proceedings Document entitled/labeled "Proces-Verbal De Constar" and its English translation, 2020.
MacoPharma Traceability Brochure entitled "Transfusion Safety of Blood Products . . . Traceability of Collection & Processing Bags", 2010.
Macoproductions Document No. M07A2025 B entitled/labeled "Soudure Filtre Monobloc colpitt pour le filter P-CAPT" and its English language translation, 2007.
TechnoPharm and Fannin Purchase Orders, 2007-2008.
MacoPharma Invoices, 2007-2008.
2010 P-CAPT Photographs, 2020.
LCRD2 LEUCOFLEX Brochure entitled "Leucocyte Reduction Filter for Red Cell Concentrate", 2014.
MacoPharma LEUCOFLEX LCR-Diamond Brochure entitled "The Optimal Solution for Maximum Haemoglobin Recovery", 2007.
LCRD Drawing entitled/labeled "FILTLCRD sur SF", 2015.
LCRD2 Drawing entitled/labeled "FILTLCRD sur SF", 2015.
MacoPharma Product Information document entitled/labeled "Technical Data : 1. Welding Process", 2003.
Document No. M07A1112 Q entitled/labeled "Mode operatoire Soudure filter Carrousel Thimonnier" and its English language translation, 2012.
Document No. M07A1132 J entitled/labeled "Mirage Des Filtres Souples En Sortie De SF" and its English language translation, 2012.
NPT6286LA Drawing entitled/labeled "Emballer Unitairement Avec Un Elastique", 2012.
MacoPharma Invoices entitled/labeled "Facture", 2013.
LCRD2 Photographs, 2012.
Document No. F07G1257 A entitled/labeled "Filtre Leucoflex® LCRD2" and its English language translation, 2010.
Foreign Language Opposition against European Patent 15 761 409.0/3 117 844 (filed Mar. 19, 2020) and English language translation thereof, and Communication of the notice of opposition, dated Mar. 26, 2020.
"Summons to attend Oral Proceedings" issued in European Patent Application No. 15761409.0 dated May 4, 2022.
Submission of Opponent issued for EP Application No. 15761409.0 (U.S. Pat. No. 3,117,844) and English language translation thereof, dated Sep. 22, 2022.
"Quality procedure MO7A1112R", dated Nov. 2012, 1 page.

(56) References Cited

OTHER PUBLICATIONS

"Quality procedure MO7A1132K", dated Jun. 2013, 1 page.
"NPT6286LA drawing—L version", dated Jun. 2012, 1 page.
"NPT6286LA drawing—M version", dated Jul., 2012, 1 page.

* cited by examiner

BLOOD TREATMENT FILTER

This is a continuation application of pending U.S. Application Ser. No. 15/124,167, filed on Sep. 7, 2016, which is a National Stage Entry of PCT/JP2015/056938, filed on Mar. 10, 2015, which claims the benefit of Japanese Patent Application No. 2014-046554, filed on Mar. 10, 2014. The entire contents of each of the above-identified documents, including the specification, drawings, and claims, is incorporated herein by reference in its entirety.

TECHNICAL FIELD

The present invention relates to a blood treatment filter for removing undesirable components, such as aggregates and leukocytes, from blood. In particular, the present invention relates to a precise and disposable blood treatment filter for removing microaggregates and leukocytes which may cause side effects from whole blood preparations, erythrocyte preparations, thrombocyte preparations, blood plasma preparations and the like for blood transfusion, as well as a method of manufacturing the blood treatment filter.

BACKGROUND ART

It is becoming common for whole blood collected from a donor to be separated into blood component preparations, such as an erythrocyte preparation, a thrombocyte preparation, and a blood plasma preparation, and stored and then provided for transfusion. Since microaggregates and leukocytes included in these blood preparations cause various side effects of blood transfusion, the number of occasions for removing these undesirable components before blood transfusion and then being provided for transfusion has been increasing. Particularly, in recent years, the need for leukocyte removal has widely been recognized. The number of countries legislating application of a process of removing leukocytes from all of blood preparations for blood transfusion and subsequent use thereof for transfusion has been increased.

As a method of removing leukocytes from blood preparations, treating blood preparations using a leukocyte removal filter is most typical. Treating the blood preparations using the leukocyte removal filter is often performed at the bedside when a blood transfusion operation is performed. In recent years, however, in order to improve quality control of leukocyte-free preparations and the effectiveness of leukocyte removal process, it is more common, particularly in developed countries, to process the blood preparations in blood centers before storing the blood preparations (pre-storage leukocyte removal).

To collect blood from a donor, separate a plurality of blood components and store each of the blood components, typically, a blood collection-separation set has been previously used that includes two to four flexible bags, tubes for connecting these bags, anticoagulant, erythrocyte preservation solution, and a blood collection needle. Systems including the blood collection-separation set and a leukocyte removal filter integrated therein are widely used as systems that are preferably used for "pre-storage leukocyte removal" described above, and are referred to by names such as "closed systems" and "integrated systems". These systems are disclosed in Japanese Unexamined Patent Publication No. H1-320064, International Publication No. WO 92/020428 and the like.

Conventionally, a filter element made of nonwoven fabric or a porous body packed in a hard container of polycarbonate or the like has been widely used as a leukocyte removal filter. However, since the gas permeability of the container is low, there is a problem that it is difficult to apply steam sterilization, which is widely used as a sterilization process for blood collection-separation sets. In one case of the closed system, leukocytes are first removed from the whole blood preparation after blood collection, the leukocyte removal filter is separated, and then a centrifugal operation for component separation is applied. In another case, first, a plurality of blood components are separated by centrifuging the whole blood, and subsequently the leukocytes are removed. In the latter case, the leukocyte removal filter is also centrifuged together with the blood collection-separation set. At such time, there is a possibility that a hard container may damage bags and tubes, or the hard container itself may not withstand the stress and may break during centrifugation.

As a method for solving these problems, "flexible leukocyte removal filters" have been developed in which a material having excellent flexibility and steam permeability identical or similar to the material used for the bags of the blood collection-separation set is used for the container. This type of flexible leukocyte removal filters can be broadly classified into a type in which the filter element is once welded to a sheet-shaped flexible frame, and subsequently the filter is welded to a housing material (see Description of European Patent No. 0526678), and a type in which a flexible container is directly welded to the filter element (see Japanese Unexamined Patent Publication No. H7-267871 and International Publication No. WO 95/017236). Hereinafter, the former is sometimes referred to as a frame welding type and the latter is sometimes referred to as a container welding type.

Typically, in the case of treating blood with these types of leukocyte removal filters, a bag that contains a blood preparation to be treated and is connected to a blood inlet side of the filter via a tube is placed at a height that is approximately 20 to 100 cm above the filter to allow the blood preparation to pass through the filter by the action of gravity. The filtered blood preparation is stored in a recovery bag connected to a blood outlet side of the filter via a tube. During filtration, a pressure loss occurs due to the resistance of the filter element, whereby the pressure in a space on the inlet side of the filter becomes a positive pressure. In the case of the filter that includes a flexible container, there is a tendency for the flexibility of the container itself to cause the container to swell like a balloon due to the positive pressure, thereby pressing the filter element against the container on the outlet side.

Furthermore, typically, a bag for storing blood having been processed with the blood filter is placed at a position that is 50 to 100 cm lower than the filter. Since blood moves through a flow path on the downstream side due to the action of gravity, there is a tendency for the outlet side of the filter to become a negative pressure, and the flexible container is prone to be in close contact with the filter element.

That is, it has been pointed out previously that a filter adopting a flexible container has a problem in that there is a strong tendency for the filter element to be in close contact with the outlet-side container due to the dual force, and thus the flow of blood is impeded and an adequate filtering flow rate cannot be obtained.

To address this problem, what includes a blood flow path at the periphery of a space on a blood outlet side of a filter element and also includes a tubular blood outflow port around the blood flow path has been proposed (Japanese Unexamined Patent Publication No. H11-216179). Thus, blood is favorably introduced into the blood outflow port. Consequently, reduction in filtering flow rate can be prevented.

CITATION LIST

Patent Literature

[Patent Literature 1] Japanese Unexamined Patent Publication No. H01-320064
[Patent Literature 2] International Publication No. WO 92/020428
[Patent Literature 3] Description of European Patent No. 0526678
[Patent Literature 4] Japanese Unexamined Patent Publication No. H07-267871
[Patent Literature 5] International Publication No. WO 95/017236
[Patent Literature 6] Japanese Unexamined Patent Publication No. H11-216179

SUMMARY OF INVENTION

Technical Problem

Unfortunately, the blood treatment filter including the conventional blood flow path cannot sufficiently prevent reduction in filtering flow rate.

Thus, the present invention has an object to provide a blood treatment filter that can prevent reduction in filtering flow rate.

Solution to Problem

As a result of diligent research by the present inventors to solve the problems, the inventors have found that the reduction in filtering flow rate can be prevented by sealing the filter element in a state of being compressed to form a gap region which is to serve as a blood flow path, arranging at least a part of the opening of a tubular outlet port to overlap with the gap region, and resultantly providing the opening in the gap region to be allowed to communicate, and reached an aspect of the present invention.

That is, the present invention is a blood treatment filter that comprises: a sheet-shaped filter element; an inlet-side flexible container and an outlet-side flexible container that are sealed, with the filter element being interposed therebetween; an inlet port provided toward the inlet-side flexible container side with respect to the filter element; and a tubular outlet port provided toward the outlet-side flexible container side with respect to the filter element, wherein blood introduced from the inlet port and treated by the filter element is discharged from the outlet port. The blood treatment filter comprises: an outlet-side frame sheet disposed between the filter element and the outlet-side flexible container; a first seal portion provided by sealing at least the filter element and the outlet-side frame sheet in a belt-shaped manner; and an annular second seal portion provided by sealing at least the inlet-side flexible container, the outlet-side frame sheet, the outlet port, and the outlet-side flexible container in this order to surround the first seal portion. Furthermore, on the outlet side of this filter element, a valley portion is formed by the filter element being compressed at the first seal portion, the outlet port includes a protruding portion that protrudes to an inside of the outlet-side flexible container, and the protruding portion is provided with an opening at least a part of which overlaps with the first seal portion and which can communicate with a gap region formed by the valley portion. Note that, blood according to the present invention includes blood preparations, such as whole blood preparations, erythrocyte preparations, thrombocyte preparations and blood plasma preparations, for blood transfusion. Furthermore, capability of communication according to the present invention refers to, when a state in which blood is flowing is assumed, or when blood is actually flowing, a continuous gap where the outlet-side flexible container and another element are not in close contact with each other can be formed.

In the blood treatment filter, the filter element is compressed on the outlet side of the filter element to form the valley portion. Consequently, a sufficient gap region can be easily secured in comparison with the case with no valley portion. The outlet port includes a protruding portion that protrudes to the inside of the outlet-side flexible container, and at least a part of an opening formed at the protruding portion overlaps with the valley portion. As a result, the opening of the outlet port is provided to be allowed to communicate with the gap region. Consequently, even if a double force due to the positive pressure on the inlet side and the negative pressure on the outlet side is applied, reduction in filtering flow rate is prevented.

Furthermore, in the blood treatment filter, the opening may be formed at a distal end of the protruding portion disposed in the outlet-side flexible container. By providing the opening at the distal end of the protruding portion, even if the side wall of the protruding portion comes into contact with the filter element, the outlet-side frame sheet or the outlet-side flexible container, the opening is resistant to being blocked by these members, and the blood can be appropriately discharged.

Furthermore, in the blood treatment filter, at least a part of the opening formed at the distal end of the protruding portion may be provided on an inclined slope that intersects with a plane orthogonal to an axis of the outlet port. All the parts of the opening may be provided on the inclined slope. This can increase the opening area in comparison with the case where all the parts of the opening are provided on a plane orthogonal to the axis of the outlet port, assuming that the inner diameter of the protruding portion is the same. Consequently, reduction in filtering flow rate can be easily prevented.

Furthermore, the opening formed at the distal end of the protruding portion may include an extending region that protrudes toward the second seal portion. Furthermore, the extending region may extend to the proximity of the second seal portion, and be provided adjacent to the second seal portion. These facilitate collection of blood remaining in a gap residing from the valley portion toward the second seal portion.

A part of the distal end of the protruding portion that is farthest from the second seal portion may be disposed nearer to the outlet-side flexible container than the nearest portion. According to this configuration, the portion of the distal end of the outlet port that is nearest to the second seal portion is disposed nearer to the filter element than the farthest portion. As a result, the opening also faces the filter element. The portion farthest from the second seal portion is on the outlet-side flexible container side. Consequently, even if a negative pressure is applied and the outlet-side flexible container is deformed in a direction of coming into close contact with the filter element and the like, a part of the side wall that includes the farthest portion interferes with the deformation of the outlet-side flexible container. As a result, the outlet-side flexible container can be effectively prevented from blocking the opening formed at the distal end of the protruding portion.

The opening of the protruding portion may be provided in the side wall instead of the distal end of the protruding portion disposed in the outlet-side flexible container. The opening formed in the side wall may be provided to face the first seal portion. If the opening of the protruding portion is provided in the side wall, at least a part of the opening overlaps with the first seal portion. Consequently, the opening can communicate with the gap region. Furthermore, the opening is thus provided to face the first seal portion, thereby allowing the opening to communicate with the gap region further securely.

Furthermore, in the protruding portion of the outlet port, an auxiliary opening(s) that does not overlap with the first seal portion may be provided in addition to the opening. Thus, the opening area can be substantially increased, which can further facilitate preventing reduction in filtering flow rate.

Furthermore, the auxiliary opening may be formed in the side wall of the protruding portion disposed in the outlet-side flexible container. Moreover, the auxiliary opening may be provided adjacent to the second seal portion. This facilitates collection of blood remaining in an area in proximity to the second seal portion.

Furthermore, the auxiliary opening may be provided apart from the outlet-side frame sheet and the outlet-side flexible container. Thus, the auxiliary opening is resistant to being blocked by the outlet-side frame sheet or the outlet-side flexible container.

Furthermore, according to the blood treatment filter, a post-filter layer for securing a flow toward the outlet port may be disposed on a side of the filter element nearer to the outlet-side frame sheet.

Furthermore, according to the blood treatment filter, in the filter element, the effective filtering area of a filtering portion may be $20 \times 10^{-4}$ $m^2$ or more and $70 \times 10^{-4}$ $m^2$ or less.

Furthermore, according to the blood treatment filter, in the filter element, the effective filtering area of a filtering portion may be $30 \times 10^{-4}$ $m^2$ or more and $60 \times 10^{-4}$ $m^2$ or less.

Furthermore, according to the blood treatment filter, an inlet-side frame sheet may be disposed between the inlet-side flexible container and the filter element.

Furthermore, in the blood treatment filter, the inlet port and the outlet port may have the same shape.

Furthermore, the blood treatment filter may be a filter that can be used with the inlet port and the outlet port being replaced with each other, as the inlet-side frame sheet is disposed between the inlet-side flexible container and the filter element, the inlet port and the outlet port have the same shape, and the inlet-side flexible container and the outlet-side flexible container are rotationally symmetrical with each other while the inlet-side frame sheet and the outlet-side frame sheet are rotationally symmetrical with each other.

Advantageous Effects of Invention

The present invention can prevent reduction in filtering flow rate.

DESCRIPTION OF EMBODIMENTS

Embodiments of the present invention are described hereunder with reference to the drawings. Note that the term, blood, described in each of the following embodiments includes blood preparations such as whole blood preparations, erythrocyte preparations, thrombocyte preparations and blood plasma preparations for blood transfusion. Furthermore, although various modes can be adopted for the external shape of the blood treatment filter, such as a rectangular shape, a disc shape, an oval disc shape, and an elliptical shape, a rectangular shape is preferable for reducing loss of materials during production. Accordingly, in the following embodiments, an example in which the blood treatment filter has a rectangular shape is described. In each diagram, the identical or corresponding portions are assigned the same symbols, and redundant description is omitted.

First Embodiment

Figure 1:
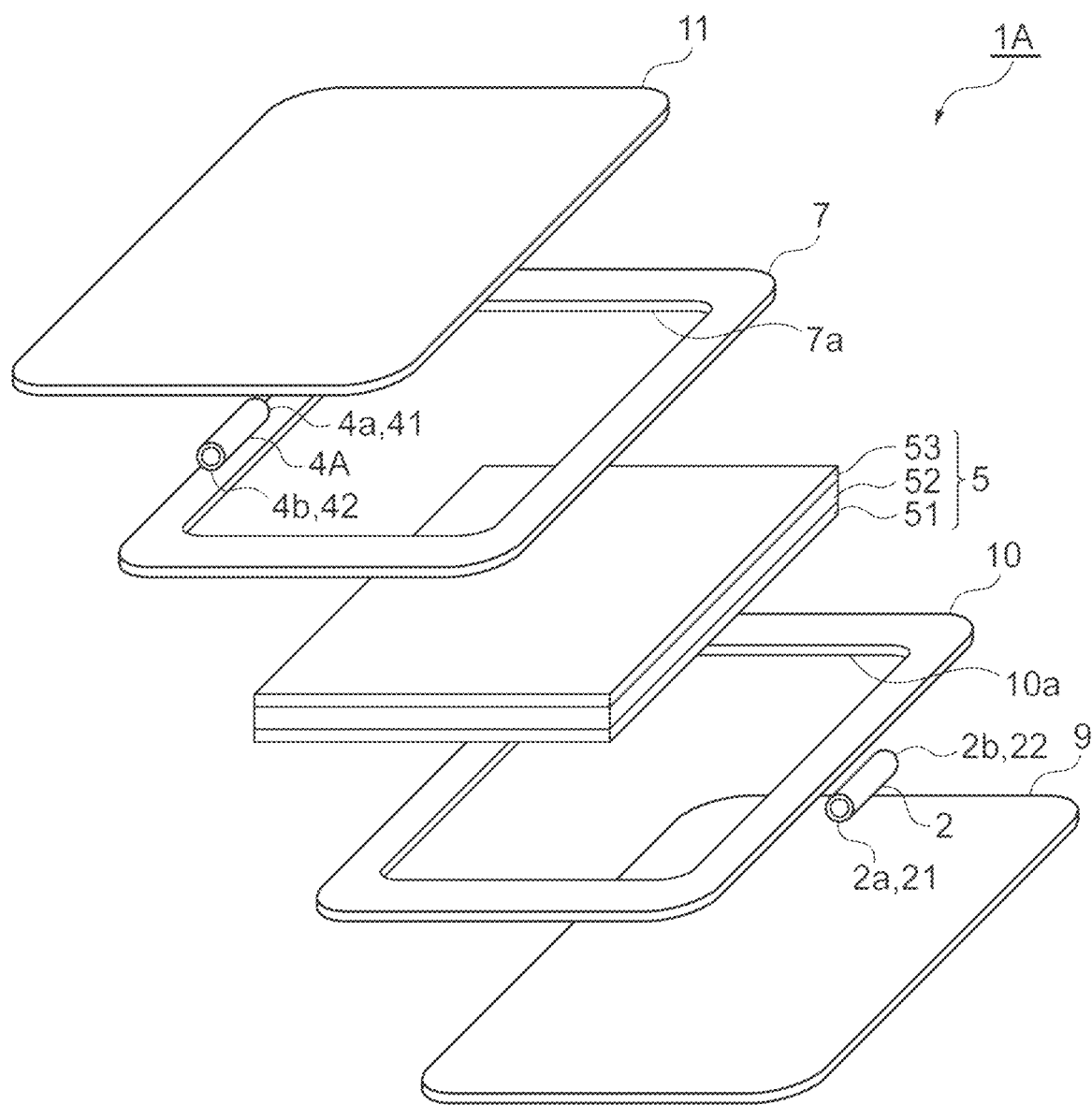
FIG. 1 is an exploded perspective view of a blood treatment filter according to a first embodiment.

First, referring to FIG. 1, members forming a blood treatment filter 1A according to a first embodiment are described. As shown in FIG. 1, the blood treatment filter 1A includes elements that are an inlet-side container (inlet-side flexible container) 9, an inlet port 2, an inlet-side frame sheet 10, a filter element 5, an outlet-side frame sheet 7, an outlet port 4A, and an outlet-side container (outlet-side flexible container) 11.

The inlet-side container 9 has a rectangular sheet shape. The inlet port 2 is tubular, and includes an internal opening (opening) 21 at one end 2a and an external opening 22 at the other end 2b. The internal opening 21 and the external opening 22 are each provided on a surface Fa that is a virtual plane orthogonal to the axis L of the inlet port 2. The inlet port 2 is provided toward the inlet-side flexible container 9 side with respect to the inlet-side frame sheet 10. When an inlet-side circuit 102 (see FIG. 6) through which blood circulates is formed, the inlet port 2 allows untreated blood to circulate from the external opening 22 into the internal opening 21, thus accepting the blood. The inlet-side frame sheet 10 has a rectangular sheet shape that has a flow path hole 10a.

The filter element 5 is disposed between the inlet-side frame sheet 10 and the outlet-side frame sheet 7. The filter element 5 has a rectangular sheet shape with a predetermined thickness. The filter element 5 has a configuration where a prefilter layer 51, a main filter layer 52, and a post-filter layer 53 are stacked in this order from the element nearer to the inlet-side container 9. The filter element 5 accepts the untreated blood introduced from the inlet port 2 into a space with the inlet-side container 9, and discharges treated blood into a space with the outlet-side container 11.

The outlet-side frame sheet 7 has a rectangular sheet shape that has a flow path hole 7a. The outlet port 4A is tubular, and includes an internal opening 41 at one end 4a and an external opening 42 at the other end 4b. The internal opening 41 and the external opening 42 are each provided on a plane Fa orthogonal to the axis L (see FIGS. 2 and 5) of the outlet port 4A. The outlet port 4A is provided toward the outlet-side flexible container 11 side with respect to the outlet-side frame sheet 7. When an outlet-side circuit 104 (see FIG. 6) through which blood circulates is formed, the outlet port 4A allows the blood treated through the filter element 5 to circulate from the internal opening 41 into the external opening 42, thus discharging the blood. The outlet-side container 11 has a rectangular sheet shape.

The inlet-side container 9 and the outlet-side container 11 are the same element. Likewise, the inlet port 2 and the outlet port 4A are the same element, and the inlet-side frame sheet 10 and the outlet-side frame sheet 7 are the same element. Note that "same element" means that at least the materials, shapes and sizes are the same.

Figure 2:
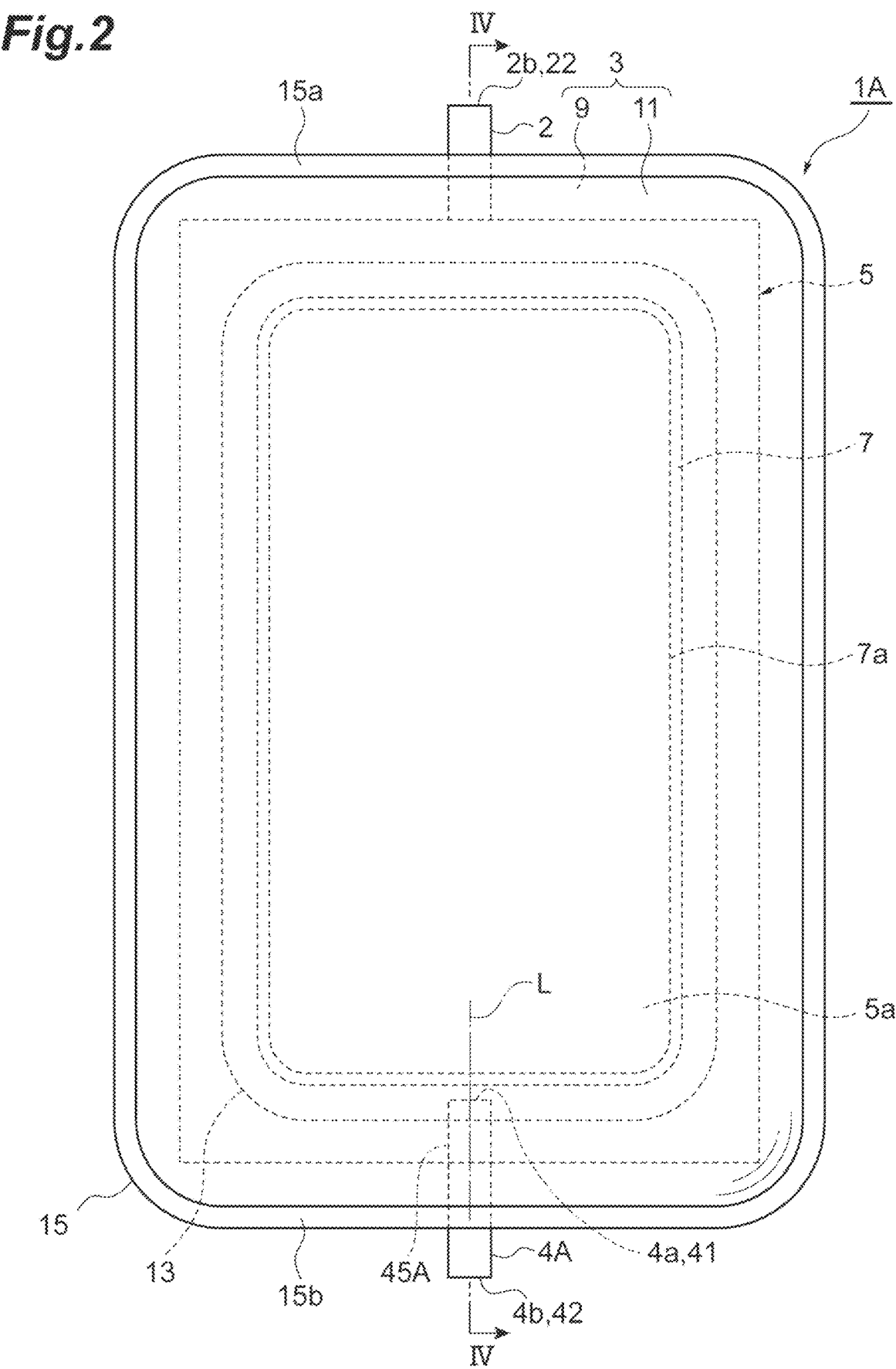
FIG. 2 is a plan view of the blood treatment filter in view from the outlet-side container.
Figure 3:
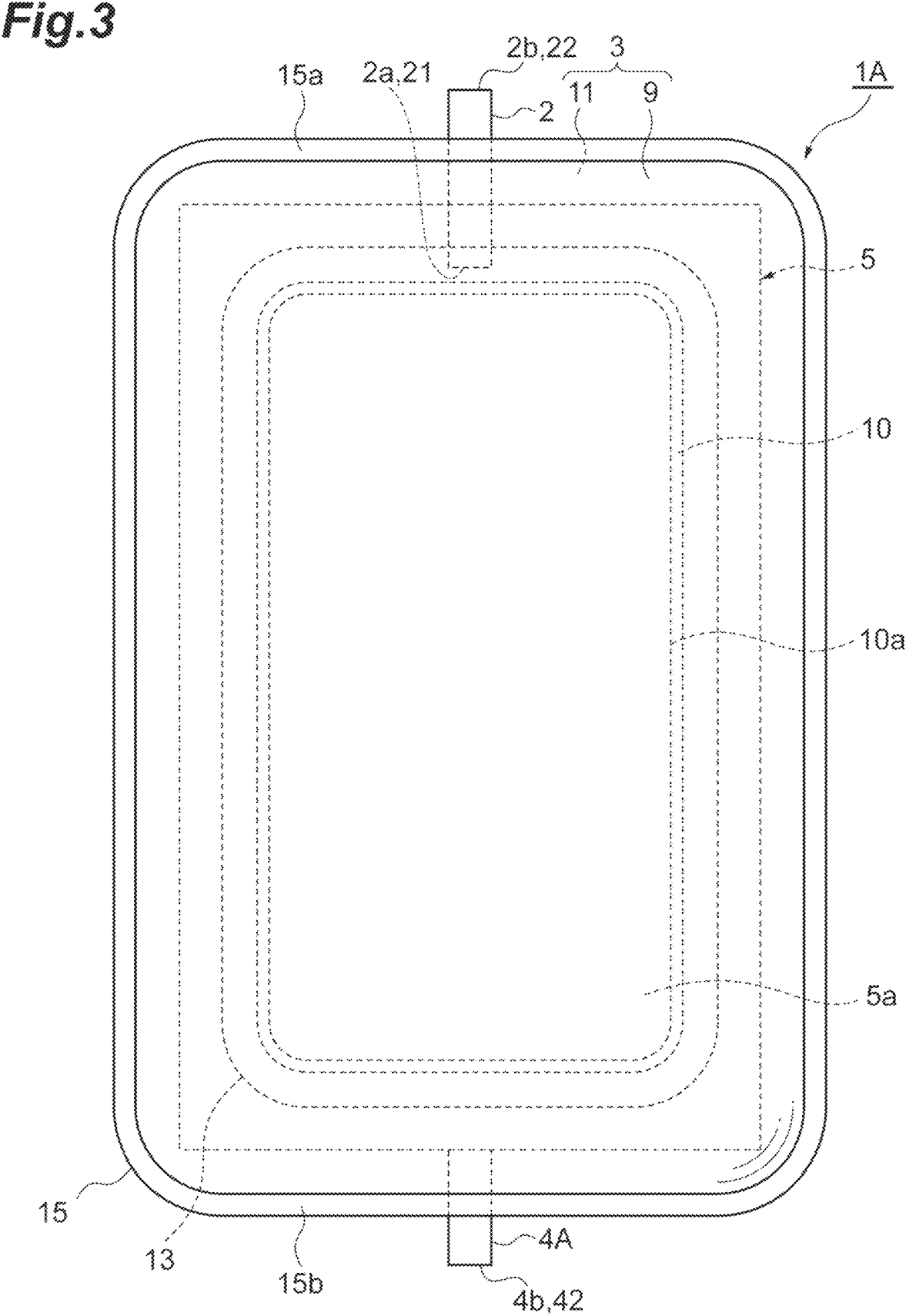
FIG. 3 is a plan view of the blood treatment filter in view from the inlet-side container.
Figure 4:
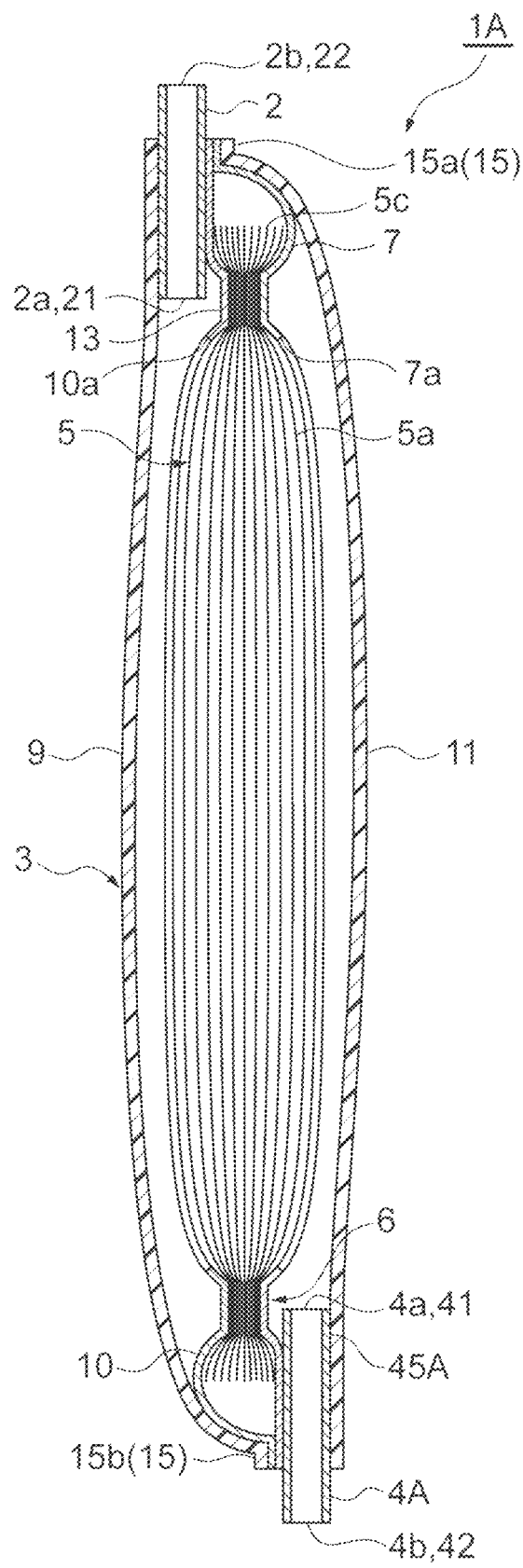
FIG. 4 is a longitudinal sectional view taken along line IV-IV of FIG. 2.

Next, referring to FIGS. 2, 3 and 4, the blood treatment filter 1A is described. The blood treatment filter 1A includes a flexible container 3. The flexible container 3 includes the inlet-side container 9 and the outlet-side container 11 that are sealed in a state where the filter element 5 is interposed therebetween. The flexible container 3 is a container having a rectangular and flat shape. Here, "flat shape" means a shape that has a small thickness and a wide area. The term, (to) seal, refers to fixing by adhesion (including welding) to an extent that can prevent liquid from leaking.

The inlet-side frame sheet 10 and the outlet-side frame sheet 7 are integrated by sealing them in a belt-shaped manner in a state such that the filter element 5 is clamped along the periphery of the filter element 5. The belt-shaped adhesive region along the periphery of the filter element 5 is an inner seal portion (first seal portion) 13. The inner seal portion 13 is provided to be apart (see FIG. 4) from each of the inlet-side container 9 and the outlet-side container 11. The inner seal portion 13 is provided not to include the peripheral edge of the filter element 5.

An area inside of the inner seal portion 13 in the flexible container 3 serves as a filtering portion that allows blood to flow, and a part of the filter element 5 facing the filtering portion serves as an effective filtering portion 5a (see FIGS. 2 to 4). The area of the effective filtering portion 5a (effective filtering area) is $20 \times 10^{-4}$ m$^2$ or more and $70 \times 10^{-4}$ m$^2$ or less, preferably, $30 \times 10^{-4}$ m$^2$ or more and $60 \times 10^{-4}$ m$^2$ or less, more preferably, $40 \times 10^{-4}$ m$^2$ or more and $55 \times 10^{-4}$ m$^2$ or less, and further preferably $40 \times 10^{-4}$ m$^2$ or more and $45 \times 10^{-4}$ m$^2$ or less. An effective filtering area smaller than $20 \times 10^{-4}$ m$^2$ causes a possibility of degrading the blood preparation collecting rate, while the area larger than $70 \times 10^{-4}$ m$^2$ causes a possibility of degrading the blood preparation collecting rate as well as increasing the filtering time. Note that a protruding nonwoven fabric portion 5c that is an end portion of the filter element 5 protrudes to the outside of the inner seal portion 13 in the flexible container 3.

The inlet-side frame sheet 10 and the outlet-side frame sheet 7 have a shape where an inside portion surrounded by the inner seal portion 13 is substantially cutoff. As a result, the flow path hole 10a and the flow path hole 7a are formed. In view of securing the effective filtering area and stably maintaining the blood flow, the end of the flow path hole 10a and the end of the flow path hole 7a cannot be too close to the inner seal portion 13. However, in case parts of the flow path hole 10a and the flow path hole 7a are overlapped (overlaid) with the inner seal portion 13, there is a possibility of impeding formation of the inner seal portion 13. Consequently, the distances between the end of the flow path hole 10a and the end of the flow path hole 7a and the inner end of the inner seal portion 13 are less than 4 mm, preferably, 0.1 or more and 3 mm or less, more preferably, 0.3 or more and 2 mm or less, further preferably, 0.5 or more and 1.5 mm or less.

The peripheries of the inlet-side container 9 and the outlet-side container 11 overlap with the peripheries of the inlet-side frame sheet 10 and the outlet-side frame sheet 7, and are sealed and integrated in a belt shape to resultantly form an rectangular and annular outside seal portion (second seal portion) 15. Although the inner seal portion 13 and the outside seal portion 15 may be formed using high frequency welding, the scope is not limited thereto. Any adhesion technique, such as ultrasonic welding or thermal welding, can be used.

The outside seal portion 15 includes an upper side portion 15a that seals the inlet port 2, and a lower side portion 15b that seals the outlet port 4A. The upper side portion 15a and the lower side portion 15b are opposite sides with respect to each other. The upper side portion 15a and the lower side portion 15b are provided so that when the blood treatment filter 1A is used, the upper side portion 15a is disposed upward and the lower side portion 15b is disposed downward.

At the upper side portion 15a, the inlet-side container 9, the inlet port 2, the inlet-side frame sheet 10, the outlet-side frame sheet 7, and the outlet-side container 11 are sealed in this order. The inlet port 2 is sealed at the center position of the upper side portion 15a. The internal opening 21 is disposed in the flexible container 3 while the external opening 22 is disposed outside of the flexible container 3.

At the lower side portion 15b, the inlet-side container 9, the inlet-side frame sheet 10, the outlet-side frame sheet 7, the outlet port 4A, and the outlet-side container 11 are sealed in this order. The outlet port 4A is sealed at the center position of the lower side portion 15b. The internal opening 41 is disposed in the flexible container 3 while the external opening 42 is disposed outside of the flexible container 3.

On the outlet side of the filter element 5 and the outlet-side frame sheet 7, the filter element 5 is compressed at the inner seal portion 13, thereby forming a valley portion 6 having a rectangular and annular shape. The inlet-side container 9 and the outlet-side container 11 do not adhere to the inner seal portion 13, and are provided so as to be apart from the inner seal portion 13 in a stationary state. Consequently, a gap region S (FIG. 5) is formed between the valley portion 6 and the outlet-side container 11.

The outlet-side container 11 has an expansion and contraction margin to some extent, but is not made of a material expandable without limitation. Consequently, even in a state where blood is flowing (outlet-side negative pressure state), formation of the valley portion 6 in proximity to the inner seal portion 13 allows a gap region S to be secured as a blood passage region without the outlet-side container 11 being adhering to and in contact with the filter element 5 and the outlet-side frame sheet 7.

Figure 5:
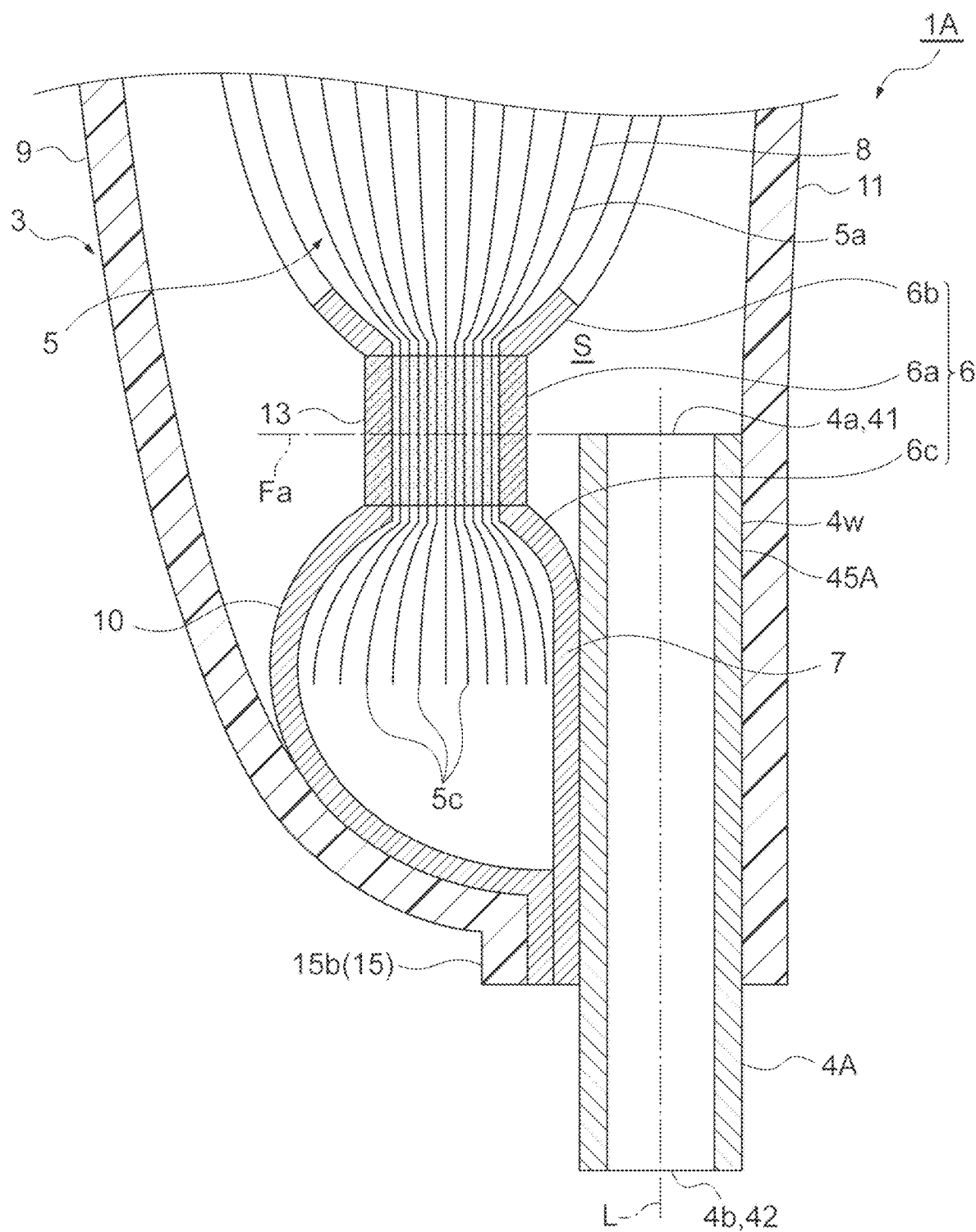
FIG. 5 is an enlarged sectional view of a valley portion.

The filter element 5 and the valley portion 6 of the outlet-side frame sheet 7 are described further in detail with reference to FIG. 5. FIG. 5 is a schematic diagram showing the filter element 5 in a stationary state, that is, a state where no blood is allowed to flow and, in particular, is a diagram schematically showing the relationship between a site for forming the valley portion 6 and other sites. The valley portion 6 includes a bottom portion 6a that overlaps with the inner seal portion 13, an internal slope portion 6b that rises from the bottom portion 6a toward the inside of the inner seal portion 13, and an external slope portion 6c that rises toward the outside of the inner seal portion 13. The internal slope portion 6b smoothly communicates with the outlet side main regional portion 8 of the filter element 5. The external slope portion 6c is a regional portion formed of a protruding nonwoven fabric portion 5c.

The formation of the valley portion 6 is herein described further in detail. The stacked filter element 5 has a certain thickness. In a state without application of processes such as welding, the surface of the filter element 5 is in a flat state. For example, when both the surfaces of the filter element 5 are clamped with PVC sheets and subjected to high frequency welding, the welded site is pressed and becomes thinner than an original thickness.

The filter element 5 according to this embodiment is subjected to high frequency welding using a predetermined mold, for example, to form the inner seal portion 13. As a result, an annular welded site is formed. Even after welding, sites other than the welded site are substantially flat as a whole. Only areas around the welded site are different. In view of the outlet side, sites adjacent to the welded site obliquely rise in the direction toward the outlet-side container 11 from the welded site, and are connected to the flat portion of the filter element 5. That is, the valley portion 6 includes the bottom portion 6a that is a region corresponding to the welded site, and the internal slope portion 6b that is a region rising obliquely from the bottom portion 6a to the inside in the direction toward the outlet-side container 11. The inner seal portion 13 is provided not to include the peripheral edge of the filter element 5. Consequently, the valley portion 6 further includes the external slope portion 6c that is a region rising obliquely from the bottom portion 6a to the outside in the direction toward the outlet-side container 11.

[Distal end of Outlet Port and Internal Opening]

The outlet port 4A is tubular and has the linear axis L. The outlet port 4A has the one end (distal end) 4a disposed in the outlet-side container 11, and the other end 4b disposed outside. The site of the outlet port 4A near the distal end 4a is a protruding portion 45A that protrudes to the inside of the outlet-side container 11. The internal opening 41 communicating with the inside of the tube is provided at the distal end 4a of the outlet port 4A (protruding portion 45A). The internal opening 41 is formed on the plane Fa orthogonal to the axis L. The distal end 4a of the protruding portion 45A is positioned just between the inner seal portion 13 and the outlet-side container 11. As a result, the internal opening 41 provided at the distal end 4a of the protruding portion 45A overlaps with the inner seal portion 13 across the entire region of the opening without extending from the inner seal portion 13 in a plan view (see FIG. 2), and can communicate with the gap region S formed by the valley portion 6. The blood filtered by passing through the filter element 5 flows through the internal opening 41 into the outlet port 4A and is discharged through the outlet port 4A.

Next, materials and shapes of elements used for the blood treatment filter 1A are described. As described above, the flexible container 3 is formed of the inlet-side container 9 and the outlet-side container 11. Any material commercially available as a sheet or a film can be utilized as a flexible resin to be used for the flexible container 3. Examples of preferable materials include thermoplastic elastomers such as soft polyvinyl chloride, polyurethane, ethylene-vinyl acetate copolymer, polyolefin such as polyethylene and polypropylene, hydrogenated styrene-butadiene-styrene copolymer, styrene-isoprene-styrene copolymer, and hydrogenated products thereof, mixtures of the thermoplastic elastomer and a softening agent such as polyolefin and ethylene-ethyl acrylate and the like. Since it can be considered that the material will be in contact with blood, preferable materials include soft polyvinyl chloride, polyurethane, and polyolefin that are used as the material of medical products such as blood bags, as well as thermoplastic elastomers containing these materials as main components, and more preferably, soft polyvinyl chloride.

Furthermore, for example, a container described in Japanese Unexamined Patent Publication No. H7-267871 or a container described in International Publication No. WO 95/017236 pamphlet can also be used as the flexible container 3.

The filter element 5 is manufactured using a filter material made of a fibrous integrated body such as nonwoven fabric or woven fabric or of a porous body such as sponge. The filter element 5 according to this embodiment may be coated with a hydrophilic polymer to enable easy wetting of the filter material with blood. Furthermore, to facilitate attachment of leukocytes to the filter element 5 in the case of using the blood treatment filter 1A to remove leukocytes from blood, a filter material coated with a polymer may be used.

In the filter element 5 (see FIG. 1), for example, the prefilter layer 51, the main filter layer 52, and the post-filter layer 53 are stacked in this order from the element nearer to the inlet-side container 9. The prefilter layer 51 is made of nonwoven fabric with an average fiber diameter of several micrometers or more and several tens of micrometers or less, and has a function of capturing microaggregates in blood. More specifically, the nonwoven fabric used for the prefilter layer 51 has an air permeability of 180 (cc/cm$^2$/sec.) or more and 300 (cc/cm$^2$/sec.) or less, and a thickness of 0.2 mm or more and 2.0 mm or less. The prefilter layer 51 is formed by stacking one or more sheets of the nonwoven fabric (e.g., two to six sheets). Here, preferably, the air permeability of the nonwoven fabric used for the prefilter layer 51 is 200 (cc/cm$^2$/sec.) or more and 280 (cc/cm$^2$/sec.) or less, and more preferably, 220 (cc/cm$^2$/sec.) or more and 260 (cc/cm$^2$/sec.) or less. Preferably, the thickness of the nonwoven fabric used for the prefilter layer 51 is 0.5 mm or more and 1.5 mm or less, and more preferably, 0.6 mm or more and 1.2 mm or less. Note that in the case of adopting relatively thin nonwoven fabric, a large number of sheets thereof are stacked to form it. In the case of adopting relatively thick nonwoven fabric, only a small number thereof are sufficient to be stacked to form it.

The main filter layer 52 is made of nonwoven fabric having an average fiber diameter smaller than the prefilter layer 51, and mainly has a function of removing leukocytes and thrombocytes. More specifically, the main filter layer 52 has an air permeability of 6.0 (cc/cm$^2$/sec.) or more and 9.0 (cc/cm$^2$/sec.) or less, and can be formed by stacking several sheets of nonwoven fabric having a thickness of 0.1 mm or more and 1.0 mm or less. Here, in the case of adopting relatively thin nonwoven fabric, a large number of sheets thereof are stacked to form it. In the case of adopting relatively thick nonwoven fabric, only a small number thereof are sufficient to be stacked to form it.

The post-filter layer 53 is made of nonwoven fabric with an average fiber diameter of several micrometers or more and several tens of micrometers or less. The post-filter layer 53 has an air permeability of 180 (cc/cm$^2$/sec.) or more and 300 (cc/cm$^2$/sec.) or less, and can be formed by stacking one or more (e.g., two or more and six or less) sheets of the nonwoven fabric having a thickness of 0.2 mm or more and 2.0 mm or less. Here, preferably, the air permeability of the nonwoven fabric used for the post-filter layer 53 is 200 (cc/cm$^2$/sec.) or more and 280 (cc/cm$^2$/sec.) or less, and more preferably, 220 (cc/cm$^2$/sec.) or more and 260 (cc/cm$^2$/sec.) or less. Preferably, the thickness of the nonwoven fabric used for the post-filter layer 53 is 0.5 mm or more and 1.5 mm or less, and more preferably, 0.6 mm or more and 1.2 mm or less. Note that in the case of adopting relatively thin nonwoven fabric, a large number of sheets thereof are stacked to form it. In the case of adopting relatively thick nonwoven fabric, only a small number thereof are sufficient to be stacked to form it. The post-filter layer 53 is disposed on the outlet-side frame sheet 7 side, and has a function of securing the flow toward the outlet port 4A. The prefilter layer 51 and the post-filter layer 53 may be the same. Note that the filter element 5 may be a single filter layer.

The inlet-side frame sheet 10 and the outlet-side frame sheet 7 can be manufactured using the same material as that of the flexible container 3, and the flow path hole 10a and the flow path hole 7a can be appropriately manufactured by a punching process or another method. A typical tube made of the same material as that of the flexible container 3 may be used for the inlet port 2 and the outlet port 4A.

[Blood Treatment System]

Figure 6:
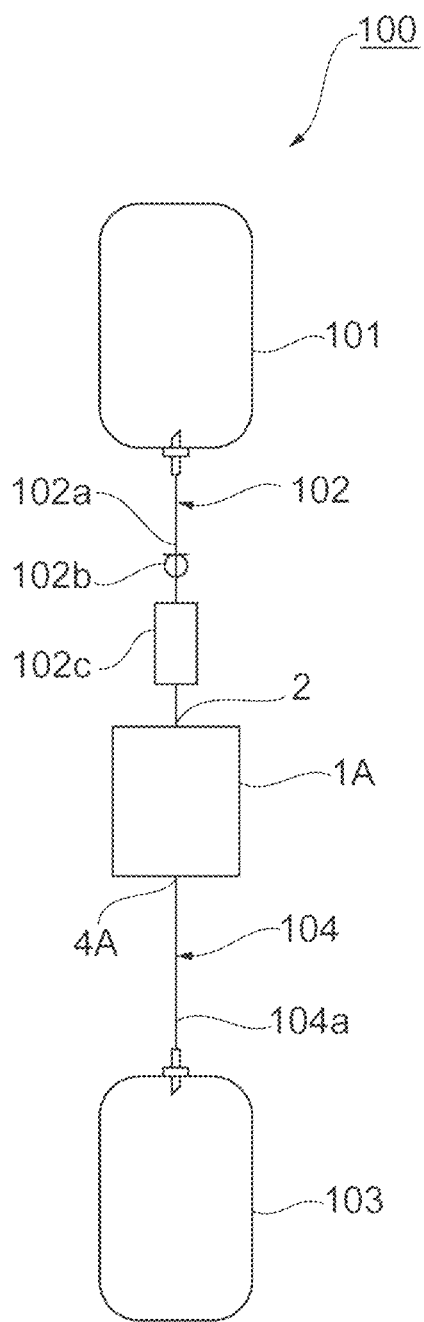
FIG. 6 is a front view that schematically shows a blood treatment system that includes a blood treatment filter.

Next, a blood treatment system 100 configured by including the blood treatment filter 1A according to the first embodiment is described with reference to FIG. 6. FIG. 6 is a front view that schematically shows the blood treatment system.

The blood treatment filter 1A can be used for filtering using gravity. For example, the blood treatment system 100 to which the blood treatment filter 1A is applied includes a reservoir bag 101 storing blood having been collected, the blood treatment filter 1A, and a recovery bag 103 for accumulating blood having been filtered. The reservoir bag 101 and the inlet port 2 of the blood treatment filter 1A are connected to each other by a tube 102a, such as a blood tube. The recovery bag 103 and the outlet port 4A of the blood treatment filter 1A are connected to each other by a tube 104a, such as a blood tube. Furthermore, opening/closing means 102b such as a roller clamp that opens and closes a flow path, a chamber 102c and the like are mounted in the tube 102a on the upstream side. The inlet-side circuit 102 is formed of the tube 102a, the opening/closing means 102b, the chamber 102c and the like. The outlet-side circuit 104 is formed of the tube 104a on the downstream side and the like.

The reservoir bag 101 storing blood having been collected is placed at a position that is approximately 50 cm higher than the blood treatment filter 1A. The recovery bag 103 for accumulating blood having been filtered is arranged at a position that is approximately 100 cm lower than the blood treatment filter 1A. The total head is 150 cm. A blood filtering process is performed by opening the flow path of the blood treatment system 100. While a filtering process is performed (at a time of use), a negative pressure arises on the outlet side of the flexible container 3 of the blood treatment filter 1A, and the outlet-side container 11 deforms and is prone to come into close contact with the filter element 5. However, as shown in FIG. 5, the valley portion 6 is formed on the outlet side of the filter element 5. Consequently, the gap region S (see FIG. 5) serving as a blood passage region is formed between the filter element 5 and the outlet-side container 11. Furthermore, the gap region S communicates with the internal opening 41 provided at the distal end 4a of the outlet port 4A (protruding portion 45A). Consequently, the blood flow path that makes connection from the outlet side of the filter element 5 to the outlet port 4A is not blocked and is stably maintained.

Next, the operations and advantageous effects of the blood treatment filter 1A according to this embodiment are described. In the blood treatment filter 1A, on the outlet side of the filter element 5, the filter element 5 is compressed in the inner seal portion 13, thereby forming the valley portion 6. Consequently, a sufficient gap region S tends to be easily formed between the inner seal portion 13 and the outlet-side container 11 in comparison with the case where the filter element 5 is not compressed. In particular, the valley portion 6 includes the internal slope portion 6b and the external slope portion 6c on the opposite sides of the bottom portion 6a. Consequently, the gap region S that is more sufficient tends to be easily formed in comparison with the case where only one of the internal slope portion 6b and the external slope portion 6c is included. The tubular outlet port 4A includes the protruding portion 45A that protrudes to the inside of the outlet-side container 11. The internal opening 41 formed at the protruding portion 45A is provided to be allowed to communicate with the gap region S. Consequently, even if the positive pressure on the inlet side and the negative pressure on the outlet side apply a double force during filtration, reduction in filtering flow rate can be prevented.

On the contrary, for example, the invention described in Patent Literature 6, the opening of the blood outflow port does not overlap with the welded portion between the filter element and the sheet-shaped frame, and the filter element is welded to the sheet-shaped frame at the peripheral edge (paragraph 0043, FIGS. 3 and 4). Thus, in the filter element described in Patent Literature 6, no valley portion is formed because the filter element is compressed at the welded portion, and a slope is formed only at an inner part of the welded portion owing to the thickness of the filter element. Consequently, the gap region secured by the invention described in Patent Literature 6 is not sufficient.

In the blood treatment filter 1A of this embodiment, the inlet-side container 9 and the outlet-side container 11 have the same shape, and rotationally symmetrical with each other. The inlet-side frame sheet 10 and the outlet-side frame sheet 7 have the same shape, and are rotationally symmetrical with each other. Furthermore, the inlet port 2 and the outlet port 4A have the same shape, and are arranged to be rotationally symmetrical with each other. In addition, in the filter element 5, the prefilter layer 51 and the post-filter layer 53 are the same. Consequently, the outlet-side container 11 and the inlet-side container 9 can be used in an inverted manner, that is, in a manner where the inlet port 2 and the outlet port 4A are replaced with each other. This allows use without consideration of the outlet and inlet. Furthermore, the number of types of component materials is reduced, thereby allowing the manufacturing process to be simplified.

In the blood treatment filter 1A of this embodiment, the internal opening 41 is provided at the distal end 4a of the outlet port 4A (protruding portion 45A). That is, even if a side wall 4w of the protruding portion 45A comes into contact with the filter element 5, the outlet-side frame sheet 7 or the outlet-side container 11, the internal opening 41 is not affected. Consequently, even if the double force due to the positive pressure on the inlet side and the negative pressure on the outlet side is applied, the internal opening 41 is resistant to being blocked with the outlet-side frame sheet 7 or the outlet-side container 11.

Typical tubes may be adopted as the inlet port 2 and the outlet port 4A. Consequently, the manufacturing cost can be reduced in comparison with the case of using a port having a complicated structure formed through injection molding.

In this embodiment, the entire internal opening 41 of the outlet port 4A (protruding portion 45A) overlaps with the inner seal portion 13 in a plan view. Alternatively, only with at least a part of the internal opening 41 overlapping with the inner seal portion 13, communication is allowed with the gap region S formed by the valley portion 6. Only one internal opening 41 is thus formed at the distal end 4a. Alternatively, another opening may be formed in the side wall 4w.

Second Embodiment

Figure 7:
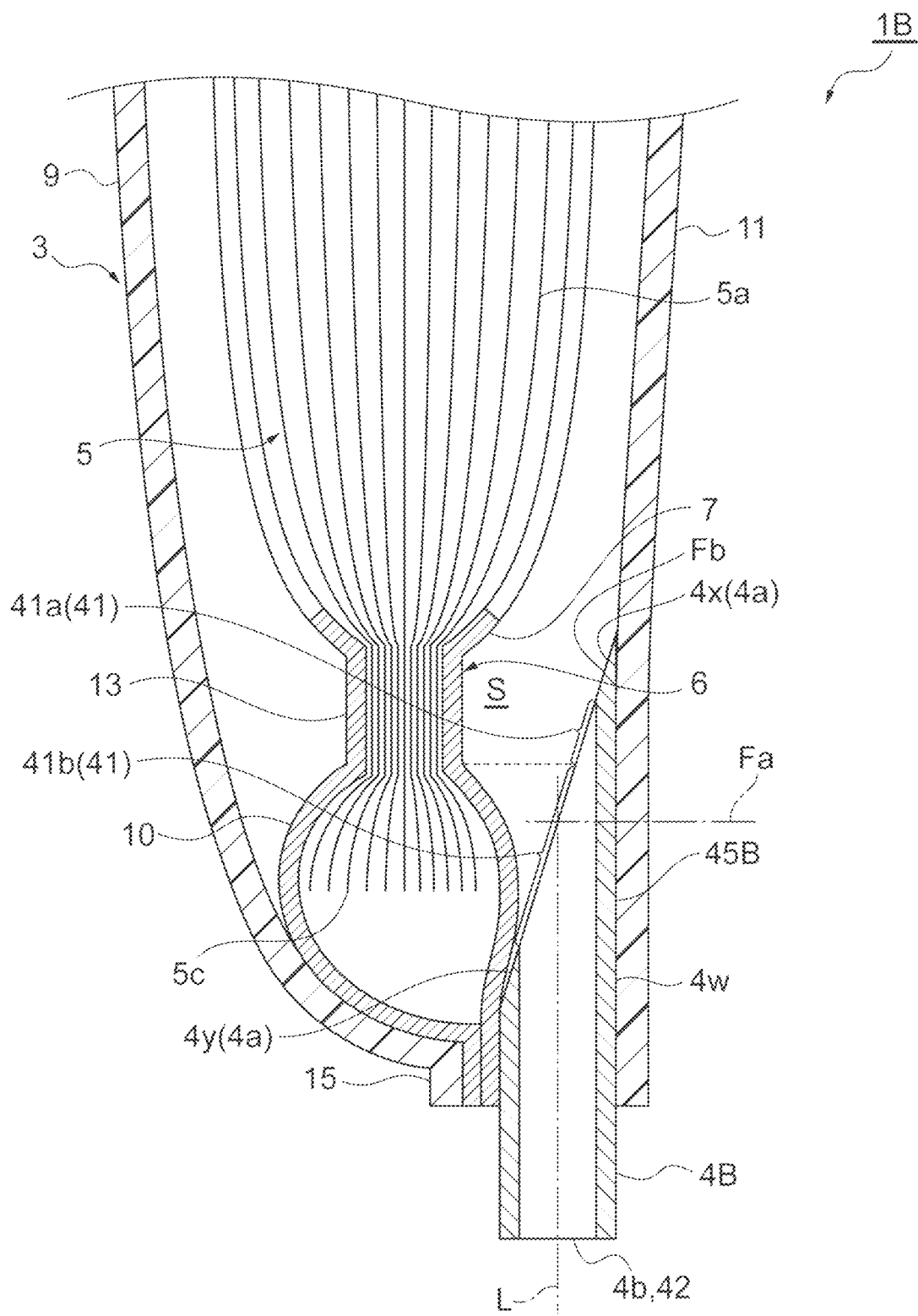
FIG. 7 is an enlarged view around an outlet port in a longitudinal sectional view of a blood treatment filter according to a second embodiment.

Next, referring to FIG. 7, a blood treatment filter 1B according to a second embodiment is described. Only the outlet port 4B of the blood treatment filter 1B is different from the outlet port 4A of the blood treatment filter 1A of the first embodiment. Other components are the same.

As shown in FIG. 7, the outlet port 4B has a shape different from that of the inlet port 2. The outlet port 4B has a protruding portion 45B that protrudes to the inside of the outlet-side container 11. An internal opening 41 is formed at the distal end 4a of the protruding portion 45B arranged in the outlet-side container 11. All the parts 41a and 41b of the internal opening 41 provided at the distal end 4a of the protruding portion 45B are provided on an inclined slope Fb inclined from the axis L of the outlet port 4B. The inclined slope Fb is an intersecting plane that intersects with the plane Fa orthogonal to the axis L of the outlet port 4B. At least apart 41a of the internal opening 41 overlaps with the inner seal portion 13 in a plan view, and can communicate with the gap region S formed with the valley portion 6.

The internal opening 41 includes a first extending region (extending region) 41b that protrudes toward the outside seal portion 15. In view of facilitating collection of blood remaining in the outlet-side container 11, the first extending region 41b cannot be too close to the outside seal portion 15. However, in case the first extending region 41b is overlapped (overlaid) with the outside seal portion 15, there is a possibility of impeding formation of the outside seal portion 15. Consequently, it is preferable that the first extending region 41b should be provided to extend close to the outside seal portion 15 and be adjacent to the outside seal portion 15. The meaning that the first extending region 41b is adjacent to the outside seal portion 15 is that the first extending region 41b and the outside seal portion 15 are in contact with each other with no overlap or with a slight gap even if a gap intervenes. Preferably, the gap is 3.0 mm or less, and more preferably, the gap is 2.5 mm or less, 2.0 mm or less, 1.5 mm or less, or 1.0 mm or less.

A farthest portion 4x of the distal end 4a farthest from the outside seal portion 15 in a direction along the axis L is disposed to be in contact with the outlet-side container 11. A nearest portion 4y is disposed to be in contact with the outlet-side frame sheet 7.

Differences of the operations and advantageous effects of the blood treatment filter 1B according to this embodiment from those of the blood treatment filter 1A of the first embodiment are described. In the blood treatment filter 1B, the internal opening 41 provided at the distal end 4a of the outlet port 4B (protruding portion 45B) is provided on a slope Fb inclined from the axis L of the outlet port 4B. Thus, the opening area can be increased, thereby allowing reduction in filtering flow rate to be sufficiently prevented.

In this embodiment, all the parts of internal opening 41 formed at the distal end 4a is provided on the inclined slope Fb inclined from the axis L of the outlet port 4B. Consequently, the opening area can be increased and reduction in filtering flow rate can be easily prevented in comparison with the case where the entire internal opening 41 is provided on the plane Fa orthogonal to the axis L. This advantageous effect can be achieved only if at least a part of the internal opening 41 is provided on the inclined slope Fb intersecting with the plane Fa orthogonal to the axis L of the outlet port 4B. For example, a part of the internal opening 41 may be formed on the inclined slope Fb, and the other parts may be on the plane Fa orthogonal to the axis L of the outlet port 4B. Consequently, in the case where the distal end 4a has a shape cut off stepwise, the internal opening 41 may have a shape where parts on the plane Fa orthogonal to the axis L and parts on the inclined slope Fb may be disposed alternately.

The internal opening 41 protrudes toward the outside seal portion 15, and has the first extending region 41b adjacent to the outside seal portion 15. Consequently, blood remaining on the outside seal portion 15 side is more easily collected than that on the inner seal portion 13 side. More specifically, the first extending region 41b is provided adjacent to the outside seal portion 15. Consequently, the collection efficiency of remaining blood is further increased.

The farthest portion 4x from the outside seal portion 15 in the distal end 4a is disposed in contact with the outlet-side container 11. The nearest portion 4y is disposed in contact with the outlet-side frame sheet 7. In case the outlet-side container 11 is deformed in a direction of coming into close contact with the filter element 5, a part of the side wall 4w of the farthest portion 4x interferes with deformation of the outlet-side container 11. As a result, a gap tends to be easily formed between the outlet-side container 11 and the outlet-side frame sheet 7 and filter element 5. Consequently, reduction in filtering flow rate can be prevented. The internal opening 41 faces the filter element 5. Consequently, the opening is resistant to being blocked, and is facilitated to communicate with the gap region S.

In this embodiment, the farthest portion 4x in the distal end 4a from the outside seal portion 15 is disposed to be in contact with the outlet-side container 11. The nearest portion 4y is disposed in contact with the outlet-side frame sheet 7. However, the disposition is not limited to this. For example, if the farthest portion 4x is disposed nearer to the outlet-side container 11 than the nearest portion 4y, close contact of the outlet-side container 11 to the filter element 5 during filtration to cause the internal opening 41 to be blocked with the outlet-side container 11 can be prevented more than a little.

In this embodiment, the internal opening 41 consists of the part 41a overlapping with the inner seal portion 13 and the first extending region 41b. However, the configuration is not limited to this. For example, as described in the following third embodiment, the configuration may include a second extending region 41c (see FIG. 8) protruding toward the effective filtering portion 5a of the filter element 5, or consist of the part 41a overlapping with the inner seal portion 13 and the second extending region 41c, or consist only of the part 41a overlapping with the inner seal portion 13.

In this embodiment, the outlet port 4B and the inlet port 2 may have the same shape; as with the blood treatment filter 1A according to the first embodiment, the configuration may be formed where the outlet-side container 11 and the inlet-side container 9 can be replaced with each other, that is, the inlet port 2 and the outlet port 4B can be replaced with each other and used.

Third Embodiment

Next, referring to FIG. 8, a blood treatment filter 1C according to a third embodiment is described. Only the outlet port 4C of the blood treatment filter 1C is different from the outlet port 4A of the blood treatment filter 1A of the first embodiment. Other components are the same.

Figure 8A:
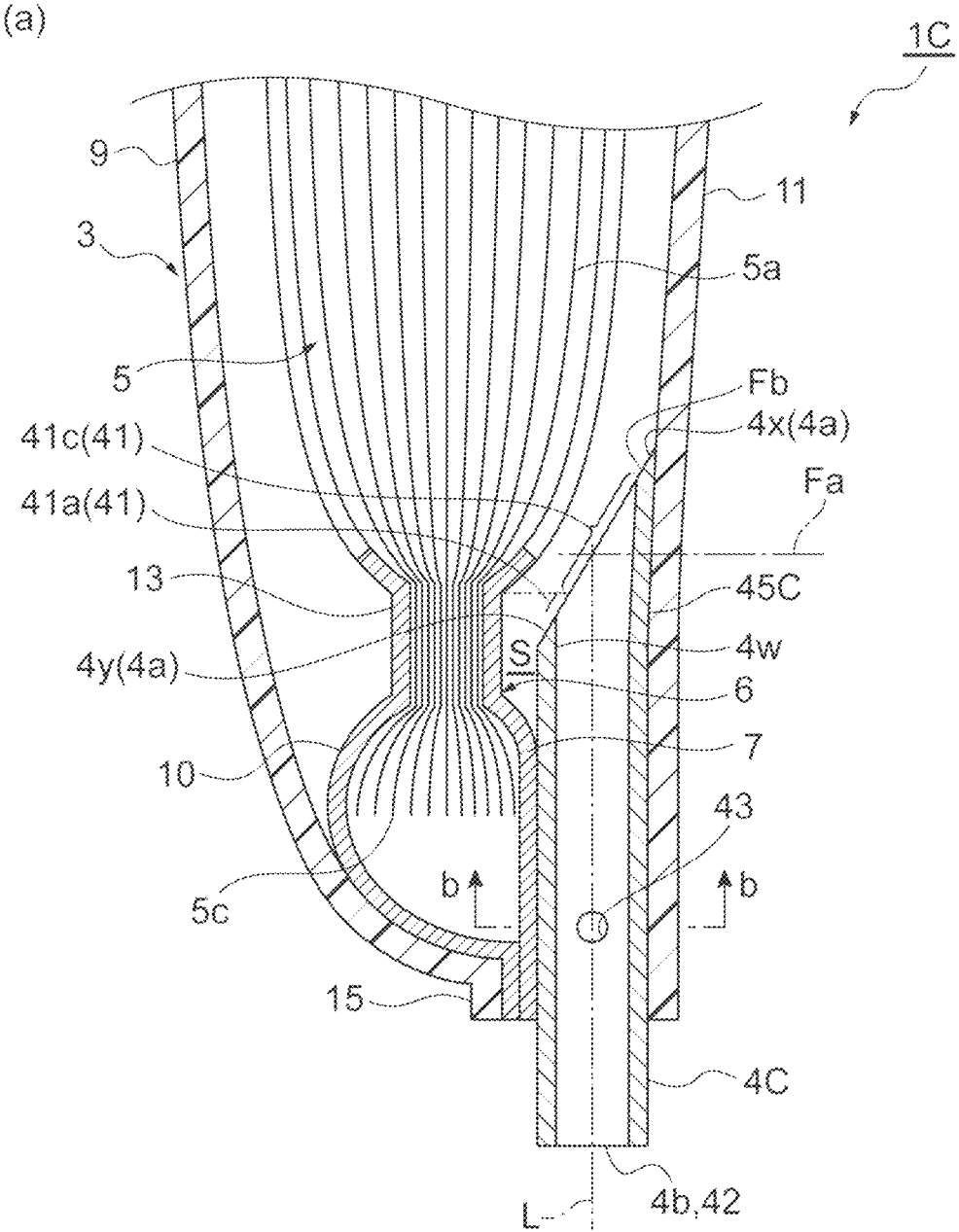
FIG. 8(a) is an enlarged view around an outlet port in a longitudinal sectional view of a blood treatment filter according to a third embodiment.

As shown in FIG. 8(a), the outlet port 4C has a shape different from that of the inlet port 2. The outlet port 4C has a protruding portion 45C that protrudes to the inside of the outlet-side container 11. An internal opening 41 is formed at the distal end 4a of the protruding portion 45C arranged in the outlet-side container 11. All the parts of the internal opening 41 provided at the distal end 4a of the protruding portion 45C are provided on an inclined slope Fb inclined from the axis L of the outlet port 4C. At least apart 41a of the internal opening 41. overlaps with the inner seal portion 13 in a plan view, and can communicate with the gap region S formed with the valley portion 6.

The internal opening 41 includes a second extending region 41c that protrudes toward the effective filtering portion 5a of the filter element 5. A farthest portion 4x of the distal end 4a farthest from the outside seal portion 15 in a direction along the axis L is disposed to be in contact with the outlet-side container 11. A nearest portion 4y is disposed to overlap with the inner seal portion 13 in a plan view.

The outlet port 4C (protruding portion 45C) is further provided with inner auxiliary openings 43 that do not overlap with the inner seal portion 13 in a plan view. The inner auxiliary openings 43 are provided adjacent to the outside seal portion 15 on the side wall 4w of the outlet port 4C (protruding portion 45C). In view of facilitating collection of remaining blood, the inner auxiliary openings 43 cannot be too close to the outside seal portion 15. However, in case the inner auxiliary openings 43 are overlapped (overlaid) with the outside seal portion 15, there is a possibility of impeding formation of the outside seal portion 15. Consequently, it is preferable that the inner auxiliary openings 43 are provided not to overlap with but to be adjacent to the outside seal portion 15. The meaning that the inner auxiliary openings 43 are adjacent to the outside seal portion 15 is that the inner auxiliary openings 43 and the outside seal portion 15 are in contact with each other with no overlap or with a slight gap even if a gap intervenes. Preferably, the gap is 3.0 mm or less, and more preferably, the gap is 2.5 mm or less, 2.0 mm or less, 1.5 mm or less, or 1.0 mm or less.

Figure 8B:
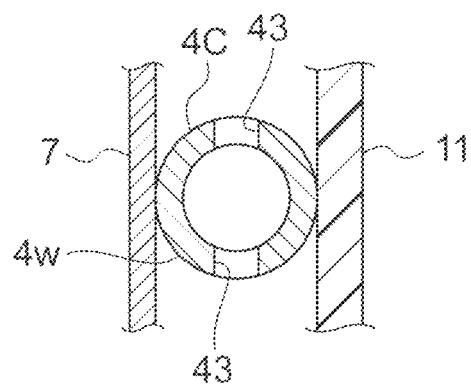
FIG. 8(b) is a sectional view taken along line b-b of FIG. 8(a).

As shown in FIG. 8(b), the inner auxiliary openings 43 are formed at two sites to be opposite to each other, in the side wall 4w of the outlet port 4C (protruding portion 45C) disposed in the outlet-side container 11, away from portions facing the outlet-side frame sheet 7 and the outlet-side container 11. More specifically, the pair of inner auxiliary openings 43 are provided at positions to have the same distance from the outlet-side frame sheet 7 and the outlet-side container 11. The direction in which the pair of inner auxiliary openings 43 are opposed to each other is along the outlet-side frame sheet 7 and the outlet-side container 11. As a result, there is a low possibility that the inner auxiliary opening 43 is blocked with the outlet-side frame sheet 7 or the outlet-side container 11, and the blood can be appropriately discharged.

Differences of the operations and advantageous effects of the blood treatment filter 1C according to this embodiment from those of the blood treatment filter 1B of the second embodiment are described. In the blood treatment filter 1C, the internal opening 41 provided at the distal end 4a of the outlet port 4C has the second extending region 41c protruding toward the effective filtering portion 5a of the filter element 5, and is disposed to allow the farthest portion 4x of the distal end 4a farthest from the outside seal portion 15 to be in contact with the outlet-side container 11. Thus, the farthest portion 4x reaches a position overlapping with the effective filtering portion 5a of the filter element 5 in a plan view. Consequently, the outlet-side container 11 is in close contact with the filter element 5 during filtration, thereby allowing reduction in filtering flow rate to be further prevented. That is, at the portion where the outlet port 4C intervenes, an interval of the outer diameter of the outlet port 4C or more occurs between the outlet-side container 11 and the outlet-side frame sheet 7 and filter element 5, and such a portion reaches the effective filtering portion 5a of the filter element 5.

The outlet port 4C of the blood treatment filter 1C is further provided with the inner auxiliary openings 43 on the side wall 4w at the positions adjacent to the outside seal portion 15. This facilitates collection of blood remaining in an area from the internal opening 41 toward the outside seal portion 15.

This embodiment has the two inner auxiliary openings 43. However, the number of the openings is not limited thereto. The number may be one, or three or more. At least one opening facilitates collection of the remaining blood more than a little.

In this embodiment, the farthest portion 4x in the distal end 4a from the outside seal portion 15 is disposed to be in contact with the outlet-side container 11. The nearest portion 4y is disposed to overlap with the inner seal portion 13 in a plan view. However, the disposition is not limited to this. For example, if the farthest portion 4x is disposed nearer to the outlet-side container 11 than the nearest portion 4y, close contact of the outlet-side container 11 to the filter element 5 during filtration to cause the internal opening 41 to be blocked with the outlet-side container 11 can be prevented more than a little.

In this embodiment, the internal opening 41 consists of the part 41a overlapping with the inner seal portion 13 and the second extending region 41c. However, the configuration is not limited to this. For example, as described in the second embodiment, the configuration may further include the first extending region 41b (see FIG. 7) protruding toward the outside seal portion 15, or consist of the part 41a overlapping with the inner seal portion 13 and the first extending region 41b, or consist only of the part 41a overlapping with the inner seal portion 13.

In this embodiment, the outlet port 4C and the inlet port 2 may have the same shape; as with the blood treatment filter 1A according to the first embodiment, the configuration may be formed where the outlet-side container 11 and the inlet-side container 9 can be replaced with each other, that is, the inlet port 2 and the outlet port 4C can be replaced with each other and used.

Fourth Embodiment

Figure 9:
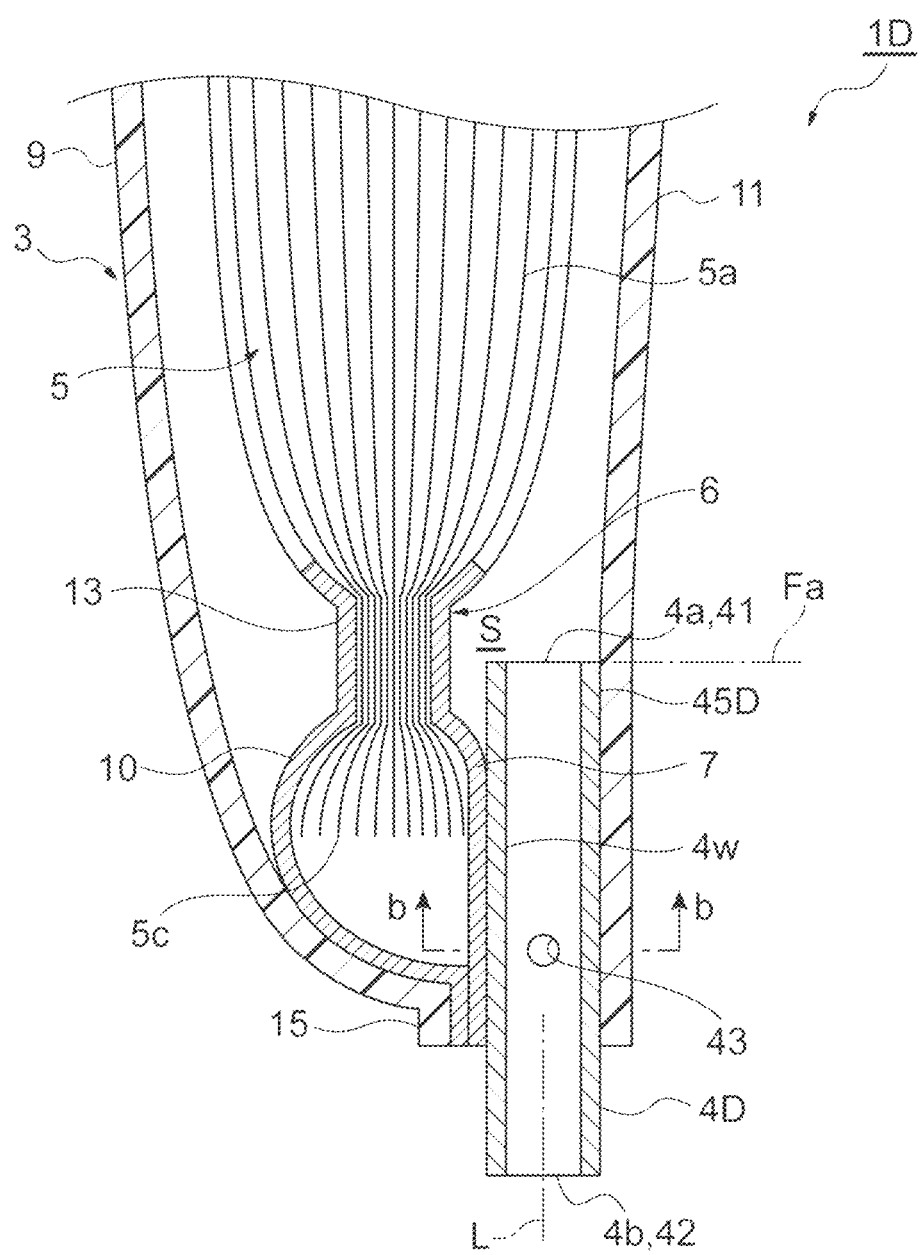
FIG. 9(a) is an enlarged view around an outlet port in a longitudinal sectional view of a blood treatment filter according to a fourth embodiment.
FIG. 9(b) is a sectional view taken along line b-b of FIG. 9(a).
Figure 9:
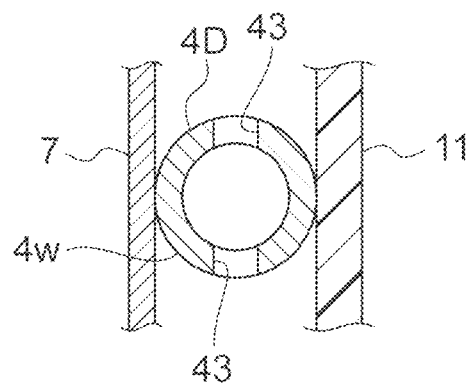

Next, referring to FIG. 9, a blood treatment filter 1D according to a fourth embodiment is described. Only the outlet port 4D of the blood treatment filter 1D is different from the outlet port 4A of the blood treatment filter 1A of the first embodiment. Other components are the same. More specifically, a difference is only in that the outlet port 4D further includes the inner auxiliary openings 43. The other points are the same.

As shown in FIG. 9(a), the outlet port 4D has a protruding portion 45D that protrudes to the inside of the outlet-side container 11. An internal opening 41 is formed at the distal end 4a of the protruding portion 45D arranged in the outlet-side container 11. The internal opening 41 provided at the distal end 4a of the protruding portion 45C is formed on a virtual plane orthogonal to the axis L, and the internal opening 41 overlaps with the inner seal portion 13 across the entire region of the opening in a plan view, and can communicate with the gap region S formed by the valley portion 6. The outlet port 4D (protruding portion 45D) includes inner auxiliary openings 43 that do not overlap with the inner seal portion 13 in a plan view. The inner auxiliary openings 43 are provided to be adjacent to the outside seal portion 15. In view of facilitating collection of remaining blood, the inner auxiliary openings 43 cannot be too close to the outside seal portion 15. However, in case the inner auxiliary openings 43 are overlapped (overlaid) with the outside seal portion 15, there is a possibility of impeding formation of the outside seal portion 15. Consequently, it is preferable that the inner auxiliary openings 43 are provided not to overlap with but to be adjacent to the outside seal portion 15.

As shown in FIG. 9(b), the inner auxiliary openings 43 are formed at two sites to be opposite to each other, in the side wall 4w of the outlet port 4D disposed in the outlet-side container 11, away from portions facing the outlet-side frame sheet 7 and the outlet-side container 11. More specifically, the pair of inner auxiliary openings 43 are provided at positions to have the same distance from the outlet-side frame sheet 7 and the outlet-side container 11. The direction in which the pair of inner auxiliary openings 43 are opposed is along the outlet-side frame sheet 7 and the outlet-side container 11. As a result, there is a low possibility that the inner auxiliary opening 43 is blocked with the outlet-side frame sheet 7 or the outlet-side container 11, and the blood can be appropriately discharged.

Differences of the operations and advantageous effects of the blood treatment filter 1D according to this embodiment from those of the blood treatment filter 1A of the first embodiment are described.

The outlet port 4D of the blood treatment filter 1D is further provided with the inner auxiliary openings 43 in the side wall 4w at the positions adjacent to the outside seal portion 15. This facilitates collection of blood remaining in an area from the internal opening 41 toward the outside seal portion 15.

This embodiment has the two inner auxiliary openings 43. However, the number of the openings is not limited thereto. The number may be one, or three or more. At least one opening facilitates collection of the remaining blood more than a little.

In this embodiment, the outlet port 4D and the inlet port 2 may have the same shape; as with the blood treatment filter 1A according to the first embodiment, the configuration may be formed where the outlet-side container 11 and the inlet-side container 9 can be replaced with each other, that is, the inlet port 2 and the outlet port 4D can be replaced with each other and used.

Fifth Embodiment

Figure 10:
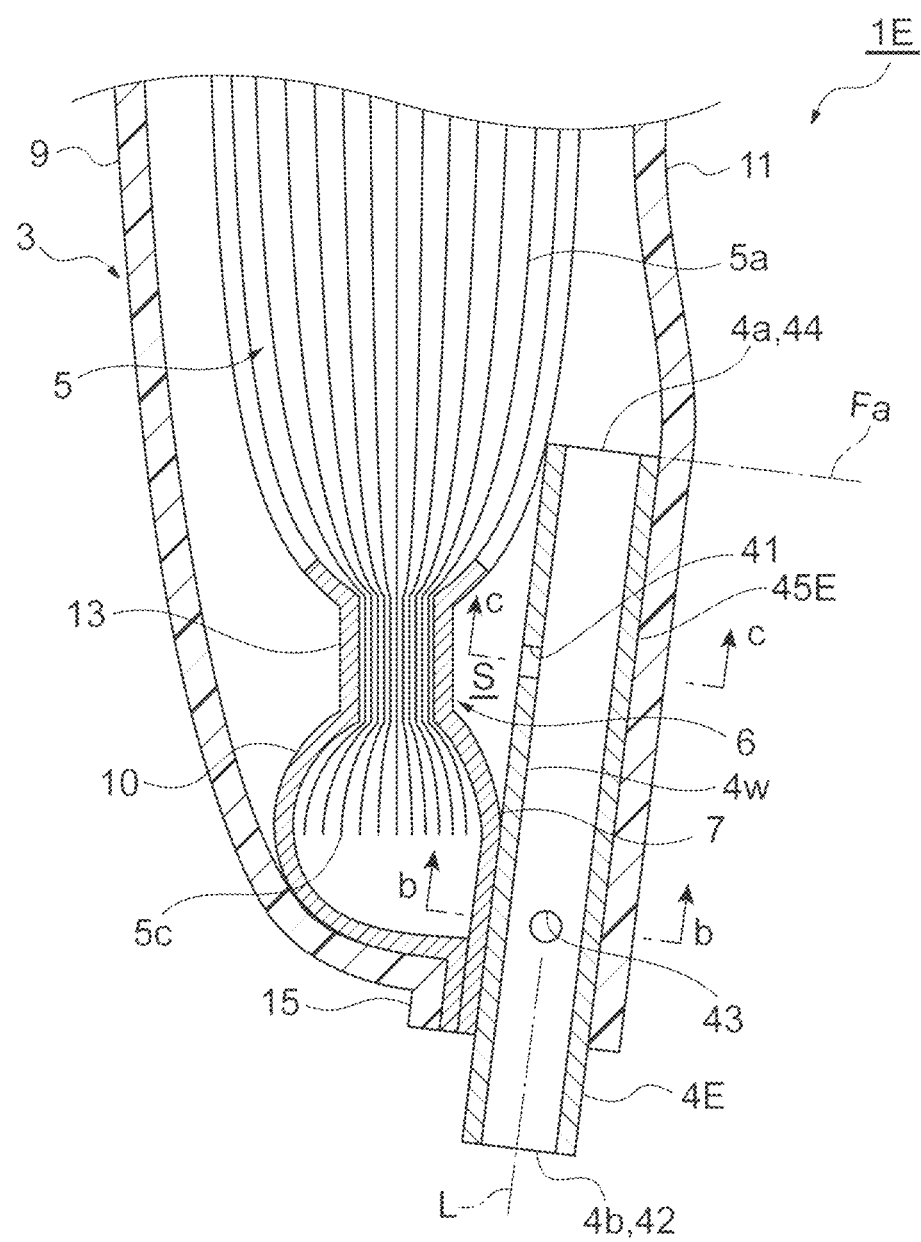
FIG. 10(a) is an enlarged view around the outlet port in a longitudinal sectional view of a blood treatment filter according to a fifth embodiment.
FIG. 10(b) is a sectional view taken along line b-b of FIG. 10(a).
FIG. 10(c) is a sectional view taken along line c-c of FIG. 10(a).
Figure 10:
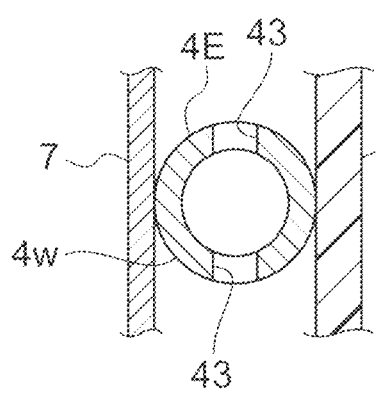
Figure 10:
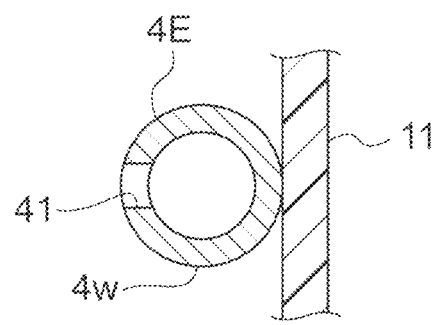

Next, referring to FIG. 10, a blood treatment filter 1E according to a fifth embodiment is described. Only the outlet port 4E of the blood treatment filter 1E is different from the outlet port 4A of the blood treatment filter 1A of the first embodiment. Other components are the same. More specifically, a difference from the outlet port 4A of the blood treatment filter 1A of the first embodiment is in that the internal opening 41 is not formed at the distal end 4a of the outlet port 4E but is formed in the side wall 4w.

As shown in FIG. 10(a), the outlet port 4E has a shape different from that of the inlet port 2. The outlet port 4E has a protruding portion 45E that protrudes to the inside of the outlet-side container 11. The internal opening 41 of the outlet port 4E (protruding portion 45E) is an opening formed in the side wall 4w, and the internal opening 41 overlaps with the inner seal portion 13 in a plan view, and can communicate with the gap region S formed by the valley portion 6 (see FIGS. 10(a) and 10(c)). That is, the internal opening 41 is disposed on a side opposite to a side in contact with the outlet-side container 11, in the side wall 4w of the outlet port 4E (protruding portion 45E) disposed in the outlet-side container 11, and resultantly is provided opposite to the inner seal portion 13.

The outlet port 4E (protruding portion 45E) is further provided with first inner auxiliary openings 43 that do not overlap with the inner seal portion 13 in a plan view (see FIGS. 10(a) and 10(b)). The first inner auxiliary openings 43 are provided to be adjacent to the outside seal portion 15. In view of facilitating collection of remaining blood, the first inner auxiliary openings 43 cannot be too close to the outside seal portion 15. However, in case the first inner auxiliary opening 43 are overlapped (overlaid) with the outside seal portion 15, there is a possibility of impeding formation of the outside seal portion 15. Consequently, it is preferable that the first inner auxiliary openings 43 are provided not to overlap with but to be adjacent to the outside seal portion 15.

The first inner auxiliary openings 43 are formed at two sites to be opposite to each other, in the side wall 4w of the protruding portion 45E disposed in the outlet-side container 11, away from portions facing the outlet-side frame sheet 7 and the outlet-side container 11. More specifically, the pair of inner auxiliary openings 43 are provided at positions to have the same distance from the outlet-side frame sheet 7 and the outlet-side container 11. The direction in which the pair of inner auxiliary openings 43 are opposed is along the outlet-side frame sheet 7 and the outlet-side container 11. As a result, there is a low possibility that the inner auxiliary opening 43 is blocked with the outlet-side frame sheet 7 or the outlet-side container 11, and the blood can be appropriately discharged.

The distal end 4a of the outlet port 4E is further provided with a second inner auxiliary opening 44 that do not overlap with the inner seal portion 13 in a plan view. The second inner auxiliary opening 44 overlaps with the effective filtering portion 5a of the filter element 5 in a plan view. The second inner auxiliary opening 44 is provided on a plane Fa orthogonal to the axis L.

Differences of the operations and advantageous effects of the blood treatment filter 1E according to this embodiment from those of the blood treatment filter 1A of the first embodiment are described.

In the blood treatment filter 1E, the internal opening 41 communicating with the gap region S is provided in the side wall 4w of the protruding portion 45E disposed in the outlet-side container 11. Consequently, even if a double force due to the positive pressure on the inlet side and the negative pressure on the outlet side is applied during filtration, the internal opening 41 can prevent reduction in filtering flow rate. Furthermore, at the distal end 4a of the outlet port 4E, the second inner auxiliary opening 44 is provided. Consequently, the total opening area increases, which can prevent reduction in filtering flow rate.

The distal end 4a of the outlet port 4E (protruding portion 45E) extends toward the effective filtering portion 5a of the filter element 5. Consequently, the outlet-side container 11 is in close contact with the filter element 5 during filtration, thereby allowing reduction in filtering flow rate to be prevented. That is, at the portion where the outlet port 4E intervenes, an interval of the outer diameter of the outlet port 4E or more occurs between the outlet-side container 11 and the outlet-side frame sheet 7 and filter element 5, and such a portion reaches the effective filtering portion 5a of the filter element 5.

The outlet port 4E of the blood treatment filter 1E is further provided with the first inner auxiliary openings 43 in the side wall 4w at the positions adjacent to the outside seal portion 15. This facilitates collection of blood remaining in an area from the internal opening 41 toward the outside seal portion 15.

This embodiment has the one internal opening 41. However, the number of the openings is not limited thereto. The number may be two or more. All the internal openings 41 may be provided in the side wall 4w of the outlet port 4E. Alternatively, one of the openings may be provided on the distal end 4a.

In this embodiment, the entire internal opening 41 overlaps with the inner seal portion 13 in a plan view. Alternatively, only with at least a part overlapping with the inner seal portion 13 in a plan view, communication is allowed with the gap region S. Furthermore, the internal opening 41 faces the inner seal portion 13. Consequently, the opening directly faces the gap region S, and the efficiency is high. However, facing the inner seal portion 13 is not a necessary requirement for allowing communication with the gap region S. To allow communication, it is sufficient that at least a part overlaps with the inner seal portion 13 in a plan view. Consequently, for example, even if the internal opening 41 does not face the inner seal portion 13 but only if the opening is provided away from the part facing the outlet-side container 11, communication is allowed with the gap region S.

The number of inner auxiliary openings 43 is two. However, the number is not limited thereto. The number may be one, or three or more. At least one opening facilitates collection of the remaining blood more than a little. The second inner auxiliary opening 44 provided at the distal end 4a of the outlet port 4E (protruding portion 45E) is thus provided on the plane Fa orthogonal to the axis L of the outlet port 4E. However, the configuration is not limited thereto. At least a part of the second inner auxiliary opening 44 may be provided on the plane Fa orthogonal to the axis L of the outlet port 4E. Thus, the opening area can be increased, thereby allowing reduction in filtering flow rate to be further prevented. Furthermore, it is preferable that in this case, the farthest portion 4x of the distal end 4a from the outside seal portion 15 (see FIG. 7) is arranged nearer to the outlet-side container 11 than the nearest portion 4y to the outside seal portion 15 (see FIG. 7).

In this embodiment, the outlet port 4E and the inlet port 2 may have the same shape; as with the blood treatment filter 1A according to the first embodiment, the configuration may be formed where the outlet-side container 11 and the inlet-side container 9 can be replaced with each other, that is, the inlet port 2 and the outlet port 4E can be replaced with each other and used.

Figure 11:
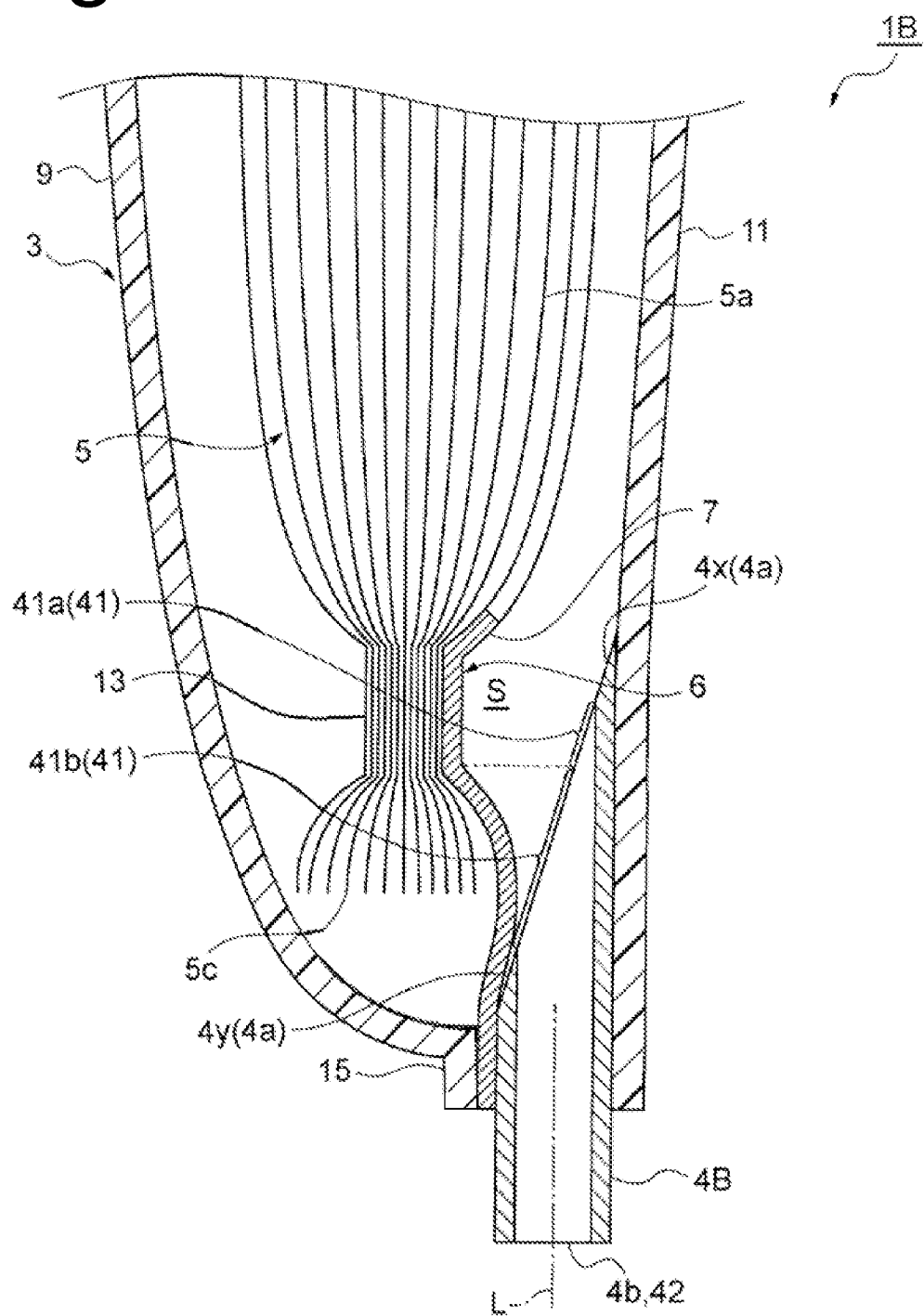
FIG. 11 is an enlarged view around an outlet port in a longitudinal sectional view of a blood treatment filter in which an inlet-side frame sheet is not shown.

FIG. 11 illustrates an enlarged view around an outlet port 4B of a blood treatment filter in which an inlet-side frame sheet is not shown.

EXAMPLES

The present invention will now be described in further detail below by way of Examples. However, the present invention should not be limited by Examples.

Example 1

Example 1 adopted a filter corresponding to the blood treatment filter 1B according to the aforementioned second embodiment. More specifically, as Example 1, a filter was used that included elements that were an inlet-side container (inlet-side flexible container), an inlet port, an inlet-side frame sheet, a filter element, an outlet-side frame sheet, an outlet port, and an outlet-side container (outlet-side flexible container). In Example 1, the inlet port of the filter was connected to a pre-filtration liquid reservoir bag via an inlet-side circuit having a length of 50 cm. The outlet port of the filter was connected to the post-filtration liquid recovery bag via an outlet-side circuit having a length of 100 cm. A tube made of soft polyvinyl chloride having an internal diameter of 2.9 mm and an external diameter of 4.2 mm was used for the inlet-side circuit and the outlet-side circuit.

For preparing the filter, an effective filtering portion was formed in a rectangular shape in which an inner side of an inner seal portion (first seal portion) had a longitudinal dimension of 74 mm and a lateral dimension of 57 mm, a corner portion was formed as a curve, and an effective filtration area of $42 \times 10^{-4}$ m$^2$ was provided. As the filter element, four sheets of polyester nonwoven fabric having an air permeability of 237.3 (cc/cm$^2$/sec.) and a thickness of 0.2 mm, one sheet of polyester nonwoven fabric having an air permeability of 8.4 (cc/cm$^2$/sec.) and a thickness of 0.4 mm, 32 sheets of polyester nonwoven fabric having an air permeability of 7.7 (cc/cm$^2$/sec.) and a thickness of 0.2 mm, one sheet of polyester nonwoven fabric having an air permeability of 8.4 (cc/cm$^2$/sec.) and a thickness of 0.4 mm, and four sheets of polyester nonwoven fabric having an air permeability of 237.3 (cc/cm$^2$/sec.) and a thickness of 0.2 mm were stacked in this order from an inlet to an outlet at the time of filtering blood, and used. Note that the air permeability was measured by a method based on Japanese Industrial Standard JIS L-1096, 6.27.1A.

The same flexible sheet with a thickness of 0.4 mm was used for the inlet-side container, the outlet-side container, the inlet-side frame sheet, the outlet-side frame sheet, and the flow path securing sheet. Tubes made of polyvinyl chloride having an internal diameter of 3.5 mm and an external diameter of 5 mm was used for the inlet port and the outlet port.

The filter element was clamped and sealed at the same time by the inlet-side frame sheet and the outlet-side frame sheet, thus forming the inner seal portion. Next, the filter element sealed with the inner seal portion to the inlet-side frame sheet and the outlet-side frame sheet was clamped between the inlet-side container and the outlet-side container. Subsequently, the inlet port was caused to interpose between the inlet-side container and the inlet-side frame sheet, was sealed (temporarily attached) and attached. Likewise, the outlet port was caused to interpose between the outlet-side container and the outlet-side frame sheet, and was sealed (temporarily attached) and attached.

Subsequently, the inlet-side container, the inlet-side frame sheet, the outlet-side frame sheet, and the outlet-side container were sealed at the same time, thus forming the outside seal portion (second seal portion). At this time, each of the site where the inlet port was sealed and the site where the outlet port was sealed was configured to be overlaid with the outside seal portion. Portions of the inlet-side frame sheet inside of the inner seal portion entirely served as flow path holes. Likewise, portions of the outlet-side frame sheet inside of the inner seal portion entirely served as flow path holes.

When the outlet port was sealed, the distal end of the outlet port (protruding portion) was disposed to overlap with the valley portion formed at the inner seal portion. Furthermore, the distal end of the outlet port (protruding portion) was configured to be inclined. That is, the internal opening at the distal end is provided on the inclined slope inclined from the axis of the outlet port. The portion of the distal end that is nearest from the outside seal portion was disposed adjacent to the outside seal portion. That is, assembly was performed such that the internal opening and the gap region at the valley portion communicated with each other, and the region of the internal opening nearest to the outside seal portion collected the entire filtered liquid in the outlet-side container without residue.

After the total head that is the total of the upstream-side head, the head between the inlet and outlet of the blood treatment filter, and the downstream-side head was fixed to 150 cm, 300 g of polyvinylpyrrolidone (weight-average molecular weight of 360000) aqueous solution prepared to have a viscosity of 17 mPa·s (25° C.) and pH 3.8 as the liquid to be treated (instead of blood) was injected into the pre-filtration liquid reservoir bag, subsequently 15 mL of air was injected, and the solution was caused to flow by gravity at room temperature. A post-filtration liquid recovery bag was preliminarily placed on an even balance to allow changes in the weight thereof to be verified.

At this time, the time required from the start of flowing the liquid to be treated until the liquid first reaching the inlet of the post-filtration liquid recovery bag was measured, and defined as a priming time (min.). Furthermore, the time required from the start of flowing the liquid to be treated until the entire liquid to be treated in the pre-filtration liquid reservoir bag being discharged, and air injected into the pre-filtration liquid reservoir bag and reaching the filter to stop increase in weight of the post-filtration liquid recovery bag due to weight conversion, that is, the time required to filter the entire liquid was measured, and defined as a total processing time (min.).

Next, the inlet of the post-filtration liquid recovery bag was oriented upward and grasped, and air accumulated by being pressed by the liquid from the inside of the system upon start of filtration and residing in the bag was pressed upward. When the entire air in the post-filtration liquid recovery bag was transferred to the filter outlet-side gap, grasping the bag is stopped, the bag was left, and the filtered liquid remaining in the filter outlet-side container was collected.

The weight of the liquid recovered in the post-filtration liquid recovery bag was measured and defined as an amount of recovery (g). An average processing speed (g/min.) was calculated on the basis of the recovery amount and the total processing time, and thus obtained. A difference between the 300 g of liquid that was injected into the pre-filtration liquid reservoir bag and the amount of recovery was obtained by calculation, and defined as amount of loss (g).

Example 2

Example 2 adopted a filter corresponding to the blood treatment filter 1D according to the aforementioned fourth embodiment. In manufacturing with the outlet port of the filter being sealed, the distal end of the outlet port (protruding portion) was held horizontally. That is, the internal opening was provided to be on a plane (perpendicular plane) orthogonal to the axis of the outlet port. At positions on the side wall of the outlet port (protruding portion) that are adjacent to the outside seal portion, the pair of auxiliary openings having a diameter of 1 mm were provided to be opposite to each other. The pair of auxiliary openings were disposed away from portions of the side wall that face the outlet-side frame sheet and the outlet-side container, and thus apart from the outlet-side frame sheet and the outlet-side container. Consequently, the openings were provided at positions that are not blocked by the outlet-side frame sheet and the outlet-side container. Except the points described above, the same method as that of the Example 1 was adopted to assemble the filter and filtering was performed.

Example 3

Example 3 adopted a filter corresponding to the blood treatment filter 1A according to the aforementioned first embodiment. In manufacturing with the outlet port of the filter being sealed, the distal end of the outlet port (protruding portion) was held horizontally. That is, the internal opening was provided to be on a plane (perpendicular plane) orthogonal to the axis of the outlet port. Except the points described above, the same method as that of Example 1 was adopted to assemble the filter and filtering is performed.

Comparative Example 1

When the outlet port of the filter according to Comparative Example 1 was sealed, the distal end of the outlet port was held horizontally. That is, the internal opening was provided to be on a plane (perpendicular plane) orthogonal to the axis of the outlet port. The distal end of the outlet port was disposed in proximity to the outside seal portion. The proximity to the outside seal portion is a region between the inner seal portion and the outside seal portion. That is, the region is a range nearer to the outside seal portion than the inner seal portion, and in a range nearer to the inner seal portion than the outside seal portion. Except the points described above, the same method as that of the Example 1 was adopted to assemble the filter and filtering is performed.

Comparative Example 2

In Comparative Example 2, tubular ports were not used as the inlet port and the outlet port, and the inlet-side frame sheet and the outlet-side frame sheet were not used. In Comparative Example 2, the inlet-side container and the outlet-side container where the inlet port and outlet port formed through injection molding were integrally provided were overlaid with each other to form the inner seal portion, and subsequently, except formation of the outside seal portion, the same method as that of Comparative Example 1 was adopted to assemble the filter, and filtration was performed.

The results of Examples 1 to 3, Comparative Examples 1 and 2 are summarized in Table 1.

TABLE 1

|  | Example 1 | Example 2 | Example 3 | Comparative Example 1 | Comparative Example 2 |
|---|---|---|---|---|---|
| Priming time (min.) | 2.8 | 2.8 | 2.8 | 2.8 | 2.3 |
| Total processing time (min.) | 17.1 | 17.2 | 17.2 | 23.4 | 26.4 |
| Amount of recovery (g) | 274.2 | 274.1 | 272.8 | 274.1 | 274.0 |
| Average processing speed (g/min.) | 16.0 | 15.9 | 15.9 | 11.7 | 10.4 |
| Amount of loss (g) | 25.8 | 25.9 | 27.2 | 25.9 | 26.0 |

Examples 1-3 have a reduced filtering time in comparison with Comparative Examples 1-2. This shows that the gap region formed by the valley portion of the inner seal portion was used as the blood passage region, and the filter element was effectively used. In blood filtration, high removing capability, such as the leukocytes removing capability, can be expected.

In Comparative Example 2, the blood flow was a flow toward the port, and the filter element was not effectively used. In Comparative Example 1, the valley portion serving as the blood passage region did not communicate with the outlet port, the outlet-side frame sheet and the outlet-side container were blocked by the negative pressure during filtration, and the filtering time was long.

REFERENCE SIGNS LIST 1A, 1B, 1C, 1D, 1E . . . Blood treatment filter, 2 . . . Inlet port, 4A, 4B, 4C, 4D, 4E . . . Outlet port, 4a . . . Distal end, 4x . . . Farthest portion, 4y . . . Nearest portion, 4w . . . Side wall, 5 . . . Filter element, 53 . . . Post-filter layer, 6 . . . Valley portion, 7 . . . Outlet-side frame sheet, 9 . . . Inlet-side container (Inlet-side flexible container), 10 . . . Inlet-side frame sheet, 11 . . . Outlet-side container (outlet-side flexible container), 13 . . . Inner seal portion (first seal portion), 15 . . . Outside seal portion (second seal portion), 41 . . . Internal opening (opening), 41b . . . First extending region (extending region), 43 . . . Inner auxiliary opening (auxiliary opening), First inner auxiliary opening (auxiliary opening), 44 . . . Second inner auxiliary opening (auxiliary opening), 45A, 45B, 45C, 45D, 45E . . . Protruding portion, L . . . Axis, S . . . Gap region, Fa . . . Plane orthogonal to axis, Fb . . . Inclined slope.

What is claimed is:

1. A blood treatment filter comprising:
an inlet-side container member and an outlet-side container member that are sealed;
a filter element, which filters blood, interposed between the inlet-side container member and the outlet-side container member and filtering blood;
an inlet port provided toward the inlet-side container member side with respect to the filter element;
a tubular outlet port provided toward the outlet-side container member side with respect to the filter element, wherein blood introduced from the inlet port is discharged from the outlet port;
an outlet-side frame sheet disposed between the filter element and the outlet-side container member;
an annular first seal portion defined by at least the filter element and the outlet-side frame sheet being adhered to each other; and
an annular second seal portion defined by the inlet-side container member, the outlet-side frame sheet, and the outlet-side container member being adhered to each other, and the outlet port being adhered to the outlet-side frame sheet and the outlet-side container member at a position where the outlet port penetrates an outer peripheral edge of the blood filter with respect to a plan view of the blood filter,
the annular second seal portion surrounding the annular first seal portion with respect to the plan view,
wherein on an outlet side of the filter element, the filter element and the outlet-side frame sheet are compressed in the first seal portion to form a valley portion that is spaced apart from the outlet-side container member,
the outlet port includes a protruding portion that is spaced apart from the valley portion and is provided with an opening at least a part of which is adjacent to the valley portion,
the opening is formed at an inclined slope relative to a central axis of the outlet port, the inclined slope forming an inclined tubular shaped peripheral edge of the protruding portion, the inclined tubular shaped peripheral edge surrounds the opening,
and a first portion of the inclined tubular shaped peripheral edge contacts the outlet-side frame sheet at a first position and a second portion of the inclined tubular shaped peripheral edge is contiguous with an inner surface of the outlet-side container member at a second position, wherein the inclined tubular shaped peripheral edge is inclined continuously from the first position to the second position so that the inclined tubular shaped peripheral edge extends across the central axis of the outlet port.

2. The blood treatment filter according to claim 1, wherein the opening is formed at an end of the protruding portion disposed in the outlet-side container member.

3. The blood treatment filter according to claim 2, wherein the opening formed on the distal end has an extending region that protrudes toward the second seal portion.

4. The blood treatment filter according to claim 3, wherein a part of the distal end that is farthest from the second seal portion is disposed in an area from the nearest portion toward the outlet-side container member.

5. The blood filter according to claim 1, wherein the opening is formed in a side wall of the protruding portion disposed in the outlet-side container member.

6. The blood filter according to claim 5, wherein the opening is provided to face the first seal portion.

7. The blood filter according to claim 1, wherein the outlet port is further provided with an auxiliary opening that does not overlap with the first seal portion.

8. The blood filter according to claim 7, wherein the auxiliary opening is formed in a side wall of the protruding portion disposed in the outlet-side container member.

9. The blood filter according to claim 8, wherein the auxiliary opening is provided to be adjacent to the second seal portion.

10. The blood filter according to claim 8, wherein the auxiliary opening is spaced apart from the outlet-side frame sheet and the outlet-side container member.

11. The blood filter according to claim 1, wherein a post-filter layer for securing a flow toward the outlet port is disposed on a side of the filter element nearer to the outlet-side frame sheet.

12. The blood filter according to claim 1, wherein in the filter element, an effective filtering area of a filtering portion is $20 \times 10^{-4}$ m$^2$ or more and $70 \times 10^{-4}$ m$^2$ or less.

13. The blood filter according to claim 1, wherein in the filter element, an effective filtering area of a filtering portion is $30 \times 10^{-4}$ m$^2$ or more and $60 \times 10^{-4}$ m$^2$ or less.

14. The blood filter according to claim 1, wherein the inlet port and the outlet port have an identical shape.

15. The blood filter according to claim 1, wherein the inclined tubular shaped peripheral edge of the protruding portion also contacts the outlet-side container member.

16. The blood filter according to claim 1, wherein the inlet port comprises a tubular shaped inlet opening which is spaced apart from the valley portion, and
    at least a part of the inlet opening is adjacent to the valley portion.

17. The blood filter according to claim 1, further comprising the outlet port penetrating the outer peripheral edge of the blood filter so as to span a distance defined between an innermost periphery of the annular second seal portion and an outermost periphery of the annular first seal portion.

* * * * *